(12) United States Patent
Onodera et al.

(10) Patent No.: US 11,974,870 B2
(45) Date of Patent: May 7, 2024

(54) X-RAY IMAGING APPARATUS

(71) Applicant: SHIMADZU CORPORATION, Kyoto (JP)

(72) Inventors: Hiroki Onodera, Kyoto (JP); Koki Yoshida, Kyoto (JP); Dai Hirose, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 63 days.

(21) Appl. No.: 17/549,416

(22) Filed: Dec. 13, 2021

(65) Prior Publication Data

US 2022/0225953 A1 Jul. 21, 2022

(30) Foreign Application Priority Data

Jan. 19, 2021 (JP) ................................. 2021-006291

(51) Int. Cl.
*A61B 6/00* (2006.01)
*A61B 6/04* (2006.01)
*G01T 1/161* (2006.01)

(52) U.S. Cl.
CPC .......... *A61B 6/4458* (2013.01); *A61B 6/0407* (2013.01); *A61B 6/544* (2013.01); *G01T 1/161* (2013.01)

(58) Field of Classification Search
CPC ... A61B 6/0407; A61B 6/4441; A61B 6/4458; A61B 6/544; A61B 6/582; A61B 6/54; A61B 6/58; A61B 6/588; A61B 6/589; A61B 6/587; A61B 6/4266; A61B 6/4464; A61B 6/4007; G01T 1/161; G01T 1/1635

See application file for complete search history.

(56) References Cited

U.S. PATENT DOCUMENTS

| | | | | |
|---|---|---|---|---|
| 4,412,346 A | * | 10/1983 | Takenouti | A61B 6/4441 378/197 |
| 6,200,024 B1 | * | 3/2001 | Negrelli | A61B 6/4476 378/197 |
| 9,642,584 B2 | * | 5/2017 | Niebler | A61B 6/4441 |
| 10,702,714 B2 | * | 7/2020 | Takeuchi | A61N 5/107 |
| 2001/0036246 A1 | * | 11/2001 | Graumann | A61B 6/51 378/197 |

(Continued)

FOREIGN PATENT DOCUMENTS

| | | |
|---|---|---|
| JP | 2001-095790 A | 4/2001 |
| JP | 2006-006471 A | 1/2006 |

(Continued)

OTHER PUBLICATIONS

Notice of Reasons for Refusal dated Dec. 5, 2023 for corresponding Japanese Patent Application No. 2021-006291.

*Primary Examiner* — Dani Fox
*Assistant Examiner* — Soorena Kefayati
(74) *Attorney, Agent, or Firm* — Muir Patent Law, PLLC

(57) ABSTRACT

This X-ray imaging apparatus includes an X-ray source, an X-ray detector, an arm, an arm driving mechanism, an X-ray detector moving mechanism, a bed, and a control unit. The control unit performs control of a position adjustment operation for adjusting a position of the X-ray detector such that a distance from a surface of a subject model serving as a model of a surface shape of the subject to the X-ray detector becomes a predetermined distance by moving the X-ray detector toward or away from the surface of the subject model.

16 Claims, 14 Drawing Sheets

(56) References Cited

U.S. PATENT DOCUMENTS

| | | | | |
|---|---|---|---|---|
| 2002/0131557 A1* | 9/2002 | Goto | A61B 6/4233 |
| | | | 378/154 |
| 2006/0256926 A1* | 11/2006 | Hiyama | A61B 6/588 |
| | | | 378/197 |
| 2008/0279340 A1* | 11/2008 | Grebner | A61B 6/588 |
| | | | 378/197 |
| 2010/0264321 A1* | 10/2010 | Blom | G01D 5/24 |
| | | | 378/65 |
| 2010/0303207 A1* | 12/2010 | Tsujii | A61B 6/4405 |
| | | | 378/197 |
| 2015/0327824 A1* | 11/2015 | Kleinszig | G06T 7/38 |
| | | | 378/62 |
| 2016/0206272 A1* | 7/2016 | Kyriakou | A61B 6/5264 |
| 2016/0220219 A1* | 8/2016 | Lalena | A61B 6/4464 |
| 2016/0278724 A1* | 9/2016 | Papaioannou | A61B 6/102 |
| 2017/0035374 A1* | 2/2017 | Schäfer | A61B 6/4441 |
| 2018/0008217 A1* | 1/2018 | Gemmel | A61B 6/4441 |
| 2018/0042571 A1* | 2/2018 | Sano | A61B 6/4035 |
| 2018/0214103 A1* | 8/2018 | Okubo | A61B 6/504 |
| 2018/0353151 A1* | 12/2018 | Tang | A61B 6/545 |
| 2019/0298275 A1* | 10/2019 | Okutani | A61B 6/0487 |
| 2020/0000418 A1* | 1/2020 | Padoy | A61B 6/547 |
| 2020/0289073 A1* | 9/2020 | Ray | A61B 6/4452 |
| 2021/0236069 A1* | 8/2021 | Kotian | A61B 6/102 |

FOREIGN PATENT DOCUMENTS

| | | |
|---|---|---|
| JP | 2006-218216 A | 8/2006 |
| JP | 2008-148866 A | 7/2008 |
| JP | 2013-255700 A | 12/2013 |
| JP | 2019-030637 A | 2/2019 |

\* cited by examiner

First imaging position

X-ray detector is distanced

First Modification

Second modification

X-RAY IMAGING APPARATUS

CROSS-REFERENCE TO RELATED APPLICATIONS

This application claims priority to Japanese Patent Application No. 2021-006291, entitled "X-Ray Imaging Apparatus," filed on Jan. 19, 2021, invented by ONODERA Hiroki, YOSHIDA Koki, HIROSE Dai, the entire contents of which is hereby incorporated by reference.

BACKGROUND OF THE INVENTION

Field of the Invention

The present invention relates to an X-ray imaging apparatus, in particular to an X-ray imaging apparatus provided with an arm for holding an X-ray source and an X-ray detector.

Description of the Background Art

Conventionally, an X-ray imaging apparatus provided with an arm for holding an X-ray source and an X-ray detector is known. Such an X-ray imaging apparatus is disclosed, for example, in Japanese Unexamined Patent Application Publication No. 2001-95790.

The X-ray imaging apparatus disclosed in Japanese Unexamined Patent Application Publication No. 2001-95790 is provided with a C-shaped arm, an X-ray tube, a flat panel X-ray detector, a slide support mechanism, a slide mechanism, and a bed. The X-ray tube is provided at one end of the C-shaped arm, and the flat panel X-ray detector is provided at the other end of the C-shaped arm. The slide support mechanism holds the flat panel X-ray detector movably in a direction orthogonal to the irradiation axis of X-rays. The slide mechanism holds the slide support mechanism movably with respect to the irradiation axis direction of X-rays. That is, the X-ray imaging apparatus disclosed in Japanese Unexamined Patent Application Publication No. 2001-95790 is configured to perform imaging from different imaging positions by moving the X-ray tube and the flat panel X-ray detector by the slide support mechanism and the slide mechanism.

Further, the X-ray imaging apparatus disclosed in Japanese Unexamined Patent Application Publication No. 2001-95790 is configured such that when performing imaging, the flat panel X-ray detector is moved closer to a subject by moving the flat panel X-ray detector in a direction perpendicular to the irradiation axis of X-rays and the irradiation axis direction of X-rays. The slide holding mechanism disclosed in Japanese Unexamined Patent Application Publication No. 2001-95790 is configured to linearly move the flat panel X-ray detector manually or electrically.

The X-ray imaging apparatus disclosed in Japanese Unexamined Patent Application Publication No. 2001-95790 is configured to bring the flat panel X-ray detector closer to a subject, based on the angle of the C-shaped arm (arm) with respect to the bed. However, in the configuration in which the X-ray detector is brought closer to the subject based on the angle of the arm with respect to the bed, the X-ray detector is brought closer to the subject, based on the distance between the X-ray detector and the bed rather than the distance between the subject and the X-ray detector.

Thus, the shape of the subject placed on the bed is not considered, and therefore, the distance between the subject and the X-ray detector may sometimes become greater than a predetermined distance. When the distance between the subject and the X-ray detector becomes greater than the predetermined distance, the distance from the X-ray source to the X-ray detector becomes greater than the predetermined distance, thereby increasing the attenuation of the dose of X-rays. As the attenuation of the dose of X-rays increases, the contrast of the resulting image decreases. For this reason, in order to suppress the decrease in the contrast of the resulting image, the irradiation dose of X-rays needs to be increased. However, increasing of irradiation dose of X-rays has the disadvantage of increasing scattered X-rays. When scattered X-rays are increased, there is a disadvantage in that the image quality of the resulting image deteriorates.

Further, it is conceivable to reduce the distance between the subject and the X-ray detector by manually moving the X-ray detector by an operator. However, there is a disadvantage in that the burden on the operator increases because the X-ray detector needs to be moved manually each time the imaging position is changed. Therefore, an X-ray imaging apparatus capable of suppressing the increase in the distance between the subject and the X-ray detector while suppressing the increase in the burden on the operator has been desired.

SUMMARY OF THE INVENTION

The present invention has been made to solve the above-described problems. It is an object of the present invention to provide an X-ray imaging apparatus capable of suppressing an increase in a distance between a subject and an X-ray detector so as not to exceed a predetermined distance while suppressing an increase in the burden on an operator.

In order to achieve the above-described object, an X-ray imaging apparatus according to one aspect of the present invention is provided with: an X-ray source configured to irradiate a subject with X-rays; an X-ray detector configured to detect the X-rays emitted from the X-ray source; an arm configured to hold the X-ray source and the X-ray detector; an arm driving mechanism configured to drive the arm; an X-ray detector moving mechanism provided on the arm to advance or retract the X-ray detector in an irradiation axis direction of the X-rays; a bed configured to place a subject thereon; and a control unit. The control unit performs control of a position adjustment operation for adjusting a position of the X-ray detector such that a distance from a surface of a subject model serving as a model of a surface shape of the subject to the X-ray detector becomes a predetermined distance by moving the X-ray detector toward or away from the surface of the subject model.

The X-ray imaging apparatus according to one aspect of the present invention includes, as described above, the control unit configured to perform control of a position adjustment operation for adjusting a position of the X-ray detector such that a distance from a surface of a subject model to the X-ray detector becomes a predetermined distance. Thus, by performing the control of the position adjustment operation, the X-ray detector is arranged at the position that is the predetermined distance from the surface of the X-ray detector. Therefore, it is possible to bring the X-ray detector closer to the subject, based on the distance between the subject and the X-ray detector, taking into account the shape of the subject placed on the bed rather than the distance between the X-ray detector and the bed.

Further, it is possible to bring the X-ray detector closer to the subject up to the predetermined distance without moving the X-ray detector by the operator. As a result, it is possible to suppress that the distance between the subject and the X-ray detector becomes larger than the predetermined distance while suppressing the increase in the burden on the operator. It should be noted that the predetermined distance denotes a concept including the case where the distance is 0 (zero). That is, the predetermined distance may also include a distance at which the X-ray detector comes into contact with the surface of the subject model.

DESCRIPTION OF THE PREFERRED EMBODIMENT

Hereinafter, some embodiments in which the present invention is embodied will be described with reference to the attached drawings.

Referring to FIG. 1 to FIG. 8, the configuration of an X-ray imaging apparatus 100 according to an embodiment of the present invention will be described.

(Configuration of X-Ray Imaging Apparatus)

First, referring to FIG. 1, the configuration of the X-ray imaging apparatus 100 according to an embodiment of the present invention will be described.

Figure 1:
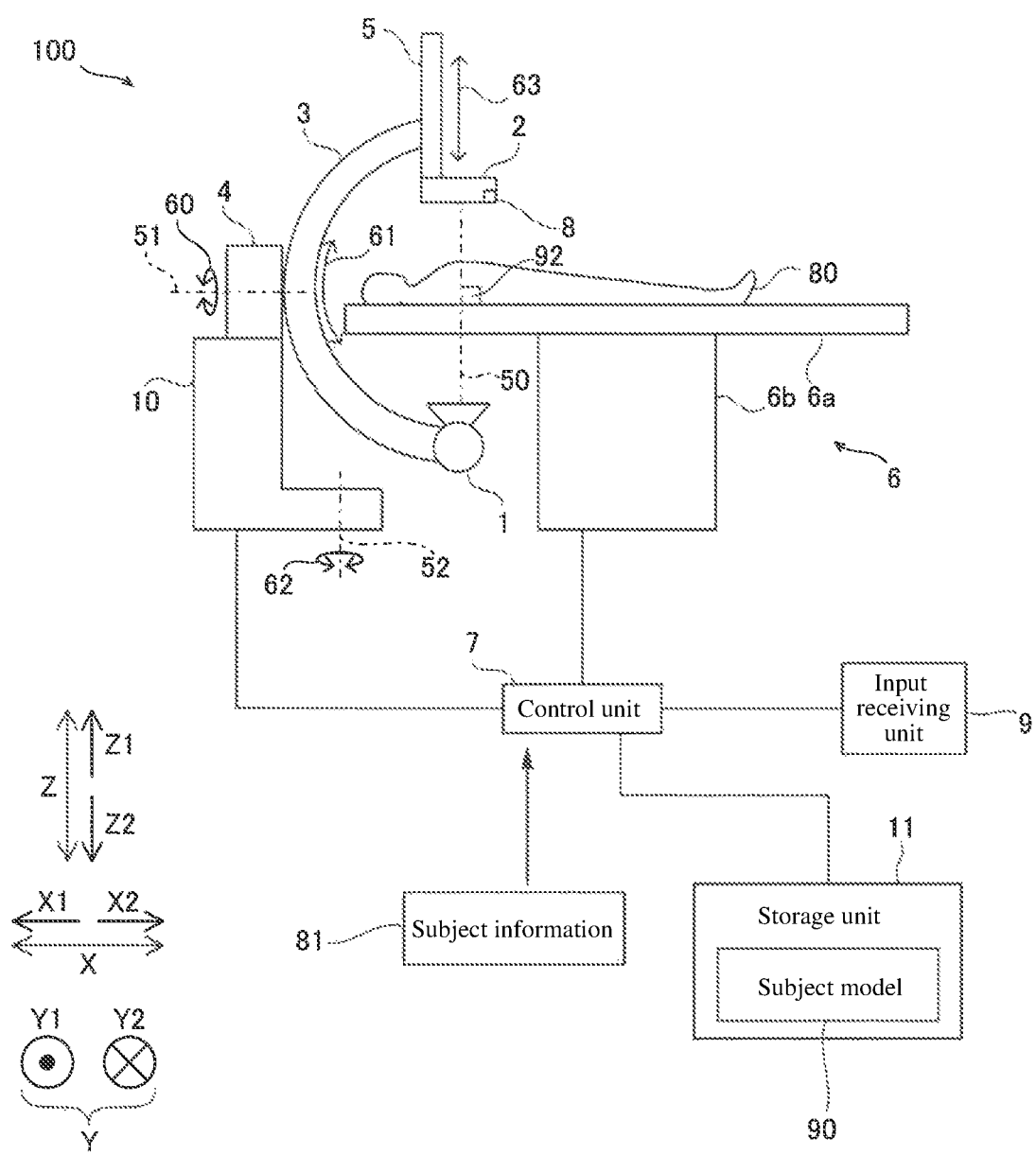
FIG. 1 is a schematic diagram illustrating the entire configuration of an X-ray imaging apparatus according to one embodiment of the present invention.

As shown in FIG. 1, the X-ray imaging apparatus 100 is provided with an X-ray source 1, an X-ray detector 2, an arm 3, an arm driving mechanism 4, an X-ray detector moving mechanism 5, a bed 6, and a control unit 7. Further, in this embodiment, the X-ray imaging apparatus 100 is further provided with a contact sensor 8. Further, in this embodiment, the X-ray imaging apparatus 100 is further provided with an input receiving unit 9. Further, in this embodiment, the X-ray imaging apparatus 100 is further provided with an arm position change mechanism 10 and a storage unit 11. In this embodiment, the X-ray imaging apparatus 100 is installed in, for example, an examination room, and a doctor or the like performs treatment and diagnostic of a region of interest of a subject 80 by capturing an image of the subject 80 by the X-ray imaging apparatus 100 with a contrast agent administered to the subject 80.

In the example shown in FIG. 1, the up-down direction is defined as a Z-direction, the upward direction is defined as a Z1-direction, and the downward direction is defined as a Z2-direction. Orthogonal directions in a horizontal plane perpendicular to the Z-direction are defined as an X-direction and a Y-direction. A direction toward one side in the X-direction is defined as an X1-direction, and a direction toward the other side in the X-direction is defined as an X2-direction. A direction toward one side in the Y-direction is defined as a Y1-direction, and a direction toward the other side in the Y-direction is defined as a Y2-direction.

The X-ray source 1 is configured to irradiate the subject 80 with X-rays. The X-ray source 1 is configured to generate X-rays when high voltage is applied based on a signal from the control unit 7 to emit the generated X-rays toward the X-ray detector 2. In the example shown in FIG. 1, the X-ray source 1 emits X-rays in the direction of the irradiation axis 50. In the example shown in FIG. 1, the X-ray source 1 is provided such that the irradiation axis extends in the Z-direction.

The X-ray detector 2 is configured to detect the X-rays emitted from the X-ray source 1. The X-ray detector 2 is configured to convert the detected X-rays to an electric signal and read the converted electric signal as an image signal. The X-ray detector 2 is, for example, an FPD (Flat Panel Detector).

The arm 3 is configured to hold the X-ray source 1 and the X-ray detector 2. In this embodiment, as shown in FIG. 1, the arm 3 has an arc-like shape and holds the X-ray source 1 at one end and the X-ray detector 2 at the other end. The arm 3 is a so-called C-shaped arm. Further, the arm 3 is held by the arm driving mechanism 4. In the example shown in FIG. 1, the arm 3 is rotatably held by the arm driving mechanism 4. In the example shown in FIG. 1, the arm 3 is arranged such that the short side of the bed 6 is positioned between the X-ray source 1 and the X-ray detector 2.

The arm driving mechanism 4 is configured to drive the arm 3. In this embodiment, as indicated by the arrow 60, the arm driving mechanism 4 rotatably holds the arm 3 about the axis of the rotation axis 51. Further, the arm driving mechanism 4 is configured to move the arm 3 in the circumferential direction of the arm 3 (in the direction of the arrow 61). The arm driving mechanism 4 includes, for example, a motor. In the example shown in FIG. 1, the arm driving mechanism 4 is configured such that the rotation axis 51 extends in the horizontal direction (X-direction).

The arm driving mechanism 4 is held by the arm position change mechanism 10 for moving the arm 3 and the arm driving mechanism 4. Specifically, the arm driving mechanism 4 is configured to change the position and the angle of the arm 3 with respect to the bed 6.

The X-ray detector moving mechanism 5 is provided on the arm 3 to advance or retract the X-ray detector 2 in the direction of the irradiation axis 50 of the X-rays. In the example shown in FIG. 1, the X-ray detector moving mechanism 5 is configured to move the X-ray detector 2 in the direction of the irradiation axis 50 of the X-rays. In the example shown in FIG. 1, since the irradiation axis 50 of X-rays extends in the Z-direction, the X-ray detector moving mechanism 5, as shown by the arrow 63, is configured to move the X-ray detector 2 in the Z-direction. The X-ray detector moving mechanism 5 includes, for example, a linear motion mechanism. The detailed configuration in which the X-ray detector moving mechanism 5 moves the X-ray detector 2 in the direction of the irradiation axis 50 of the X-rays will be described later.

The bed 6 includes a top board 6a and a top board moving mechanism 6b. A subject 80 is placed on the top board 6a. Note that the X-direction is the longitudinal direction of the top board 6a. In other words, the X-direction is the head-foot (body length) direction of the subject 80. The Y-direction is the transverse direction of the top board 6a. In other words, the Y-direction is the direction of the body width 80b (see FIG. 2) of the subject 80.

The top board moving mechanism 6b is configured to move the top board 6a under the control of the control unit 7. Specifically, the top board moving mechanism 6b is configured to move the top board 6a in the Z-direction. Further, the top board moving mechanism 6b is configured to translate the top board 6a in the XY-plane. Further, the top board moving mechanism 6b is configured to incline the top board 6a. The top board moving mechanism 6b includes, for example, a linear motion mechanism for moving the top board 6a in the X-direction, a linear motion mechanism for moving the top board 6a in the Y-direction, and a linear motion mechanism for moving the top board 6a in the Z-direction.

The control unit 7 is configured to perform the control of the X-ray imaging apparatus 100. Further, the control unit 7 is configured to perform the control of the arm driving mechanism 4 and the arm position change mechanism 10. Specifically, the control unit 7 is configured to perform the control of the position adjustment operation to adjust the position of the X-ray detector 2. Further, the control unit 7 is configured to perform the control for imaging by placing the arm 3 at a predetermined imaging position by the arm driving mechanism 4 and the arm position change mechanism 10. The control unit 7 includes, for example, a processor, such as, e.g., a CPU (Central Processing Unit). The detailed configuration in which the control unit 7 performs the control of the position adjustment operation will be described later.

The contact sensor 8 is provided on the X-ray source 1 side of the X-ray detector 2. Therefore, the contact sensor 8 is configured to detect whether or not the X-ray detector 2 and the subject 80 are brought into contact with each other. The contact sensor 8 includes, for example, a mechanical sensor.

The input receiving unit 9 is configured to accept an operation input by an operator. The input receiving unit 9 includes, for example, an input device, such as, e.g., a mouse, a keyboard, and a joystick.

The arm position change mechanism 10 is configured to move the arm driving mechanism 4 to move the arm 3 together with the arm driving mechanism 4 to the desired imaging position. The arm position change mechanism 10 is configured to be pivotable about the axis of the rotation axis 52 as indicated by the arrow 62. The arm position change mechanism 10 is configured to move the arm 3 together with the arm driving mechanism 4 to the desired imaging position by rotating about the axis of the rotation axis 52. In the example shown in FIG. 1, the arm position change mechanism 10 is configured such that the rotation axis 52 extends in the up-down direction (Z-direction).

The storage unit 11 is configured to store, for example, a subject model 90, which will be described later, and the position information on the arm 3 when imaging at each imaging position. The storage unit 11 includes a nonvolatile memory, such as, e.g., an HDD (Hard Disk Drive) and an SSD (Solid State Drive).

(Imaging Position)

In this embodiment, the X-ray imaging apparatus 100 is configured such that the control unit 7 can change the position of the arm 3 by controlling the arm driving mechanism 4 and the arm position change mechanism 10 to perform imaging at various imaging positions.

In this embodiment, imaging positions have been stored in advance in the storage unit 11. The control unit 7 is configured to perform control for automatically changing the position and the angle of the arm 3, based on the input when the operator selects the desired imaging position among the imaging positions stored in the storage unit 11. Further, the control unit 7 is configured to perform control for moving the arm 3 to any position and angle based on the operation input of the operator. This makes it possible to perform imaging at an imaging position not stored in advance.

In this embodiment, the control unit 7 is configured to change the imaging position by changing at least one of the position of the bed 6 and the position and the angle of the arm 3. In this embodiment, the control unit 7 is configured to control the top board moving mechanism 6b to move the top board 6a to thereby change the position of the bed 6. The control unit 7 is configured to control the arm driving mechanism 4 and the arm position change mechanism 10 to change the position and the angle of the arm 3. Note that the position of the bed 6 includes a position in the up-down direction (Z-direction), a position in the body axis direction (X-direction) of the subject 80, a position in the body width direction (Y-direction) of the subject 80, a position in the rotation direction about the vertical axis direction, an inclined position in the body axis direction (X-direction) of the subject 80, and an inclined position in the body width direction (Y-direction) of the subject 80. The angle of the arm 3 denotes an angle formed between the direction in which the irradiation axis 50 of X-rays extends and the direction in which the bed 6 extends. That is, the angle of arm 3 includes the angle 91 (see FIG. 5) formed between the direction in which the irradiation axis 50 of X-rays extends and the short direction (Y-direction direction) of the bed 6, and the angle 92 (see FIG. 1) formed between the direction in which the irradiation axis 50 of X-rays extends and the longitudinal direction (X-direction) of the bed 6.

The attenuation of the dose of X-rays in the space between the X-ray source 1 and the X-ray detector 2 increases as the distance between the X-ray source 1 and the X-ray detector 2 increases. Therefore, the attenuation of the dose of X-rays can be reduced as the X-ray detector 2 is moved closer to the subject 80 at the time of imaging. Therefore, in this embodiment, the control unit 7 performs control for bringing the X-ray detector 2 closer to the surface of the subject 80 in order to bring the X-ray detector 2 closer to the X-ray source 1 at each imaging position when imaging the subject 80.

Specifically, in this embodiment, the control unit 7 performs the control of the position adjustment operation so as to bring the X-ray detector 2 closer to the surface of the subject model 90, which is a model of the surface shape of the subject 80. Alternatively, the control unit 7 performs the control of the position adjustment operation such that the distance 30 (see FIG. 3) from the surface of the subject model 90 to the X-ray detector 2 becomes a predetermined distance 93 (see FIG. 3) by moving the X-ray detector 2 away from the surface of the subject model 90.

(Subject Model)

Next, referring to FIG. 2, the subject model 90 will be described. In this embodiment, the control unit 7 is configured to acquire a subject model 90. In this embodiment, the control unit 7 is configured to generate the subject model 90 based on the information 81 on the subject (see FIG. 1).

The information 81 (see FIG. 1) on the subject has been stored in, for example, a hospital system server (not shown), an electronic medical records system (not shown), etc., of a hospital in which the X-ray imaging apparatus 100 is installed. The control unit 7 acquires the information 81 on the subject stored in a hospital system server or the like via the network, a portable storage media, or the like.

The control unit 7 (see FIG. 1) is configured to acquire the body thickness 80a and the body width 80b of the subject 80 from the information 81 on the subject to generate the subject model 90. Specifically, the control unit 7 is configured to acquire the body thickness 80a and the body width 80b of the subject 80 estimated from the height and the weight of the subject 80, as the information 81 on the subject.

Further, in this embodiment, the control unit 7 (see FIG. 1) is configured to regenerate the subject model 90, based on the position of the X-ray detector 2 detected by the contact sensor 8 when the X-ray detector 2 and the subject 80 come into contact with each other. The control unit 7 is configured to acquire the body thickness 80a and the body width 80b of the subject 80 based on the position at which the X-ray detector 2 is brought into contact with the subject 80 to generate the subject model 90 based on acquired body thickness 80a and body width 80b of the subject 80.

Further, in this embodiment, the control unit 7 (see FIG. 1) is configured to generate the subject model 90, based on the body thickness level and the body width level of the subject 80 inputted by the input receiving unit 9 (see FIG. 1). The body thickness level of the subject 80 includes, for example, three levels of "large," "medium," and "small." The operator selects the body thickness level of the subject 80 based on the visual observation or the information 81 on the subject. Note that the body width level of the subject 80 includes, for example, 3 three levels of "large," "medium," and "small." The operator selects the body width level of the subject 80, based on the visual observation or the information 81 on the subject. The control unit 7 generates the subject model 90, based on the body thickness level and the body width level selected by the operator.

In this embodiment, the control unit 7 (see FIG. 1) is configured to set an imaging condition based on the dose of X-rays detected by the X-ray detector 2 and acquire the body thickness 80a and the body width 80b of the subject 80 based on the set imaging condition. In other words, in this embodiment, the control unit 7 is configured to generate the subject model 90 based on the body thickness 80a and the body width 80b of the subject 80 acquired based on the imaging condition. Here, the X-ray imaging apparatus 100 according to this embodiment performs imaging by setting the imaging condition such that the contrast of the resulting image does not change due to the body thickness 80a and the body width 80b of the subject 80. In other words, the imaging condition is set such that the dose of X-rays detected by the X-ray detector 2 is not changed by the body thickness 80a and the body width 80b of the subject 80. Therefore, the control unit 7 can acquire the body thickness 80a and the body width 80b of the subject 80 by acquiring the imaging condition. Note that the imaging condition includes the tube voltage applied to the X-ray source 1 and the tube current.

Further, for example, a table indicating the relation between the imaging condition and the body thickness 80a and the body width 80b of the subject 80, or a calibration curve, or the like is stored in the storage unit 11. The control unit 7 acquires the body thickness 80a and the body width 80b of the subject 80 from the imaging condition, based on the table or the calibration curve stored in the storage unit 11. It is unnecessary to image the subject 80 only to acquire the body thickness 80a and the body width 80b of the subject 80. It is sufficient that the control unit 7 acquires the body thickness 80a and the body width 80b of the subject 80, based on the imaging condition of the preliminary imaging or the like when the subject 80 was imaged in advance.

In this embodiment, the control unit 7 is configured to be able to select one of the following methods. The methods include: a method of generating the subject model 90 based on the information 81 on the subject; a method of generating the subject model 90 based on the position at which the X-ray detector 2 is brought into contact with the subject 80; a method of generating the subject model 90 based on the body thickness level and the body width level of the subject 80 selected by the operator; and a method of generating the subject model 90 based on the body thickness 80a and the body width 80b of the subject 80 acquired based on the imaging condition. It is configured such that the above-described methods can be performed in combination.

Further, the control unit 7 is configured such that after generating the subject model 90 based on the body thickness level and the body width level of the subject 80 selected by the operator, the X-ray detector 2 is brought into contact with the subject 80 to acquire the actual body thickness 80*a* and body width 80*b* of the subject 80 to thereby update the generated subject model 90.

Figure 2:
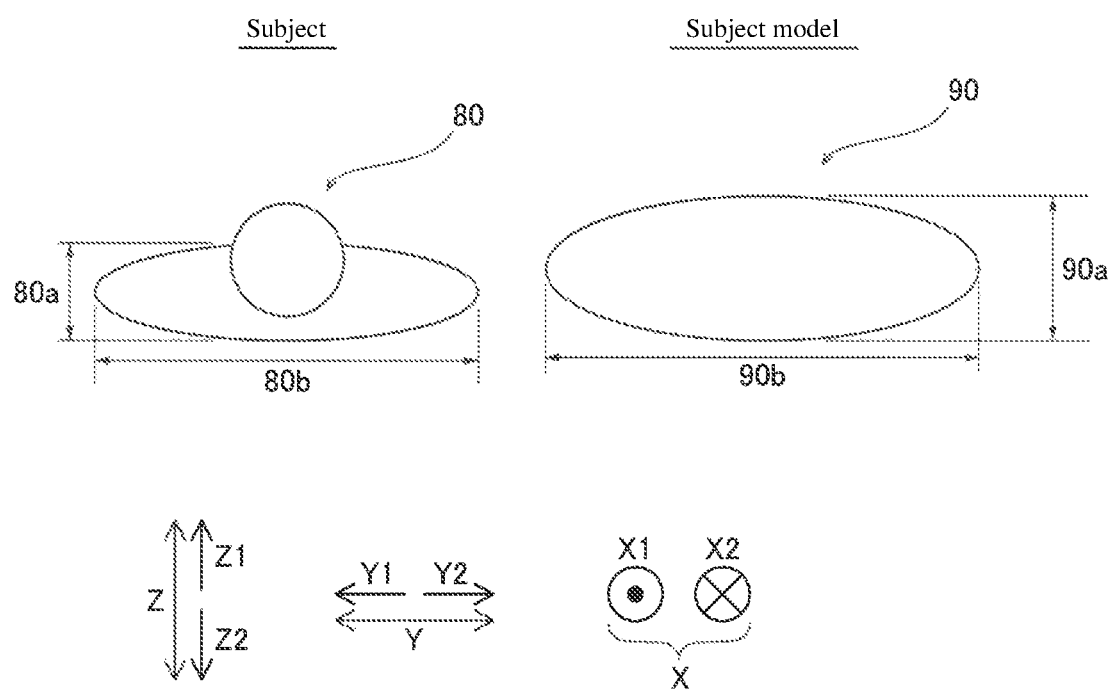
FIG. 2 is a schematic diagram for explaining a subject model generated by the X-ray imaging apparatus according to one embodiment.

As shown in FIG. 2, the control unit 7 generates, as the subject model 90, a model having an elliptical shape with a short side of a length 90*a* and a long side of a length 90*b*. The length 90*a* of the short side of the subject model 90 is larger than the body thickness 80*a* of the subject 80. Further, the length 90*b* of the long side of the subject model 90 is larger than the body width 80*b* of the subject 80. That is, the control unit 7 generates, as the subject model 90, a model having a shape larger than that of the subject 80. The subject model 90 has a shape larger than the subject 80, but the larger the shape, the greater the distance between the X-ray source 1 and the X-ray detector 2 when the X-ray detector 2 is brought close to the subject model 90. Therefore, it is preferable that the subject model 90 have a size capable of accommodating the subject 80 therein and be as small as possible.

(Control of Position Adjustment Operation)

Next, referring to FIG. 3 to FIG. 8, the control of the position adjustment operation performed by the control unit 7 in this embodiment will be described. In this embodiment, the control unit 7 performs the control of the position adjustment operation in each of the case where the arm 3 is moved automatically and the case where the arm 3 is moved manually by the operator. Note that automatically moving the arm 3 means moving the arm 3 to the predetermined imaging position by controlling the arm driving mechanism 4 and the arm position change mechanism 10 by the control unit 7 based on the imaging position inputted by the operator. Further, the case where the arm 3 is manually moved by the operator means that the control unit 7 moves the arm 3 by controlling the arm driving mechanism 4 and the position change mechanism 10 based on the operation input inputted by the operator through the input receiving unit 9.

(Position Adjustment Operation when Moving Arm Automatically)

First, referring to FIG. 3 to FIG. 7, the control of the position adjustment operation when the control unit 7 (see FIG. 1) automatically moves the arm 3 will be described.

Figure 3:
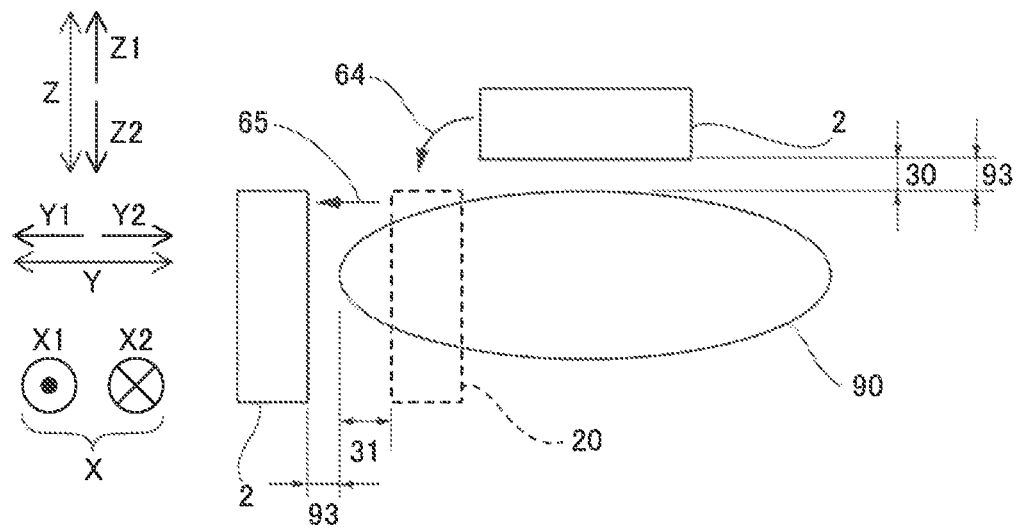
FIG. 3 is a schematic diagram for explaining a condition in which a control unit according to one embodiment performs control of a position adjustment operation.

First, referring to FIG. 3, the configuration for performing the control in which the control unit 7 retracts the X-ray detector 2 as the control of the position adjustment operation will be described. The example shown in FIG. 3 shows the case of moving the X-ray detector 2 along the arrow 64. The control unit 7 performs control for retracting the X-ray detector 2, as the control of the position adjustment operation, when the distance 30 between the X-ray detector 2 and the surface of the subject model 90 becomes the predetermined distance 93 or less at the imaging position after the change. The example shown in FIG. 3 shows the case in which the distance 30 between the X-ray detector 2 and the subject model 90 at the imaging position before the change becomes equal to the predetermined distance 93.

The example shown in FIG. 3 shows the case in which the distance 31 between the X-ray detector 2 and the surface of the subject model 90 at the imaging position after the change becomes smaller than the predetermined distance 93. Specifically, the example shown in FIG. 3 shows the case in which the X-ray detector 2 is arranged inside the subject model 90 when the X-ray detector 2 is moved to the changed imaging position. Note that in the example shown in FIG. 3, the X-ray detector 2 arranged at the imaging position after the change before performing the control of the position adjustment operation is illustrated by a broken line 20. Further, in this embodiment, the distance between the X-ray detector 2 and the subject model 90 in the case where the X-ray detector 2 is positioned outside the subject model 90 is denoted as a positive distance. Further, the distance in the case where the X-ray detector 2 is positioned inside the subject model 90 is denoted as a negative distance.

In this embodiment, the control unit 7 performs control of the position adjustment operation in a case where the distance 31 between the X-ray detector 2 and the surface of the subject model 90 at the changed imaging position after the change becomes the predetermined distance 93 or less. Specifically, when the distance 31 between the X-ray detector 2 and the surface of the subject model 90 at the imaging position after the change becomes a predetermined distance 93 or less, the control unit 7 performs control for retracting the X-ray detector 2 in the Y1-direction, as shown by the arrow 65, such that the distance 31 between the X-ray detector 2 and the surface of the subject model 90 becomes the predetermined distance 93. In a case where 0 (zero) is included in the predetermined distance 93 (when the X-ray detector 2 is brought into contact with the surface of the subject model 90), the control unit 7 performs the control of the position adjustment operation when the distance 30 between the X-ray detector 2 and the surface of the subject model 90 at the imaging position after the change becomes negative.

Figure 4:
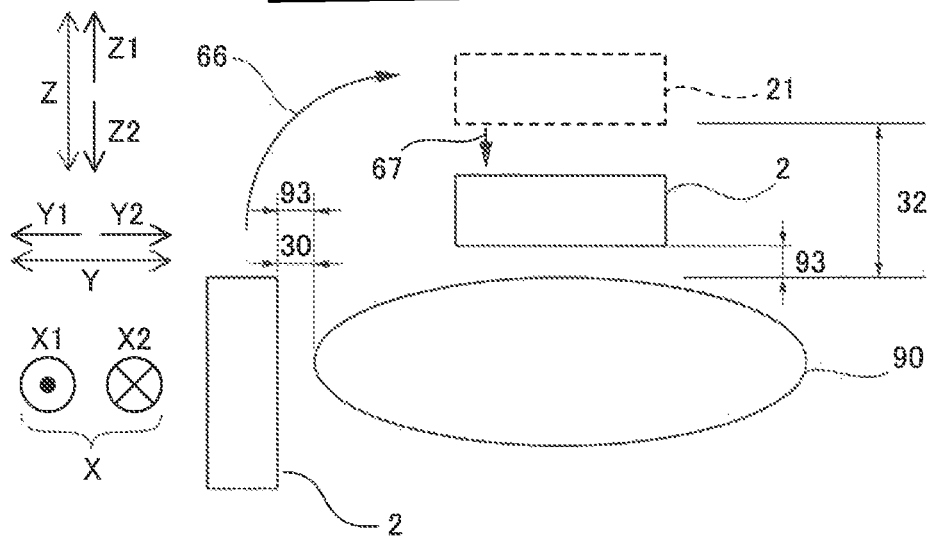
FIG. 4 is a schematic diagram for explaining a condition according to one embodiment that differs from the condition of FIG. 3 among the conditions that the control unit performs the position adjustment operation.

Next, referring to FIG. 4, an example is shown in which the control unit 7 performs control for advancing the X-ray detector 2 as the control of the position adjustment operation. The example shown in FIG. 4 shows the case of moving the X-ray detector 2 along the arrow 66. Note that in the example shown in FIG. 4, it is shown the case in which the distance 30 between the X-ray detector 2 and the subject model 90 at the imaging position becomes a predetermined distance 93.

The example shown in FIG. 4 shows the case in which the distance 32 between the X-ray detector 2 and the surface of the subject model 90 at the imaging position after the change becomes larger than the predetermined distance 93. When the distance 32 between the X-ray detector 2 and the surface of the subject model 90 at the imaging position after the change becomes greater than the predetermined distance 93, the control unit 7 performs control for advancing the X-ray detector 2 as the position adjustment operation. Note that in the example shown in FIG. 4, the position of the X-ray detector 2 at the imaging position after the change before performing the control of the position adjustment operation is shown by the broken line 21.

In the example shown in FIG. 4, as shown by the arrow 67, the control unit 7 performs the control for advancing the X-ray detector 2 in the Z2-direction such that the distance 32 between the X-ray detector 2 and the subject model 90 at the imaging position after the change becomes the predetermined distance 93.

As shown in FIG. 3 and FIG. 4, in this embodiment, when performing the control of the position adjustment operation at the time of automatically moving the arm 3, the control unit 7 acquires the distance 30 between the X-ray detector 2 and the surface of the subject model 90. In a case where the acquired distance between the X-ray detector 2 and the surface of the subject model 90 becomes the predetermined size or less, the control unit 7 is configured to perform control for retracting the X-ray detector 2. That is, in a case where the acquired distance between the X-ray detector 2 and the surface of the subject model 90 becomes the predetermined distance 93 or less, the control unit 7 is configured to perform control for retracting the X-ray detector 2. Note that the predetermined distance 93 can be set to any value by the operator.

Further, in a case where the acquired distance 30 between the X-ray detector 2 and the surface of the subject model 90 becomes a predetermined distance or more, the control unit 7 is configured to perform control for moving the X-ray detector 2. That is, in a case where the acquired distance 30 between the X-ray detector 2 and the surface of the subject model 90 becomes the predetermined distance 93 or more, the control unit 7 is configured to perform control for moving the X-ray detector 2.

Figure 5:
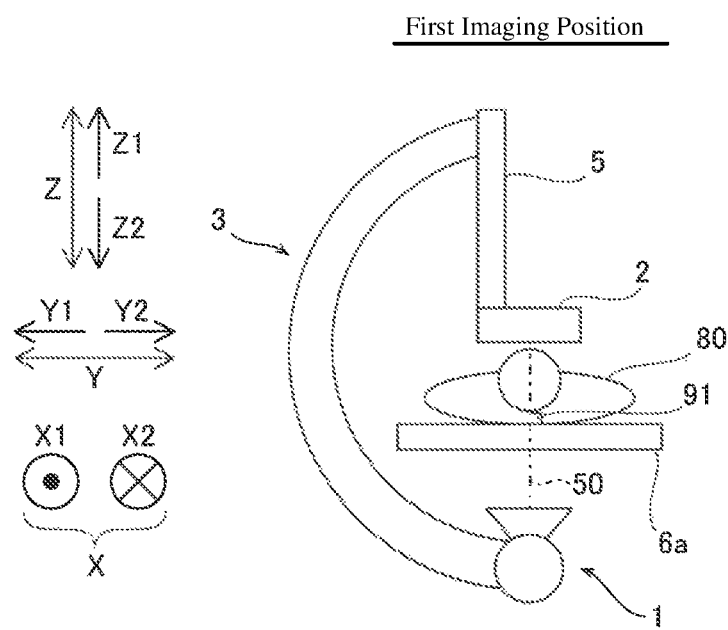
FIG. 5 is a schematic diagram for explaining a first imaging position.
Figure 6:
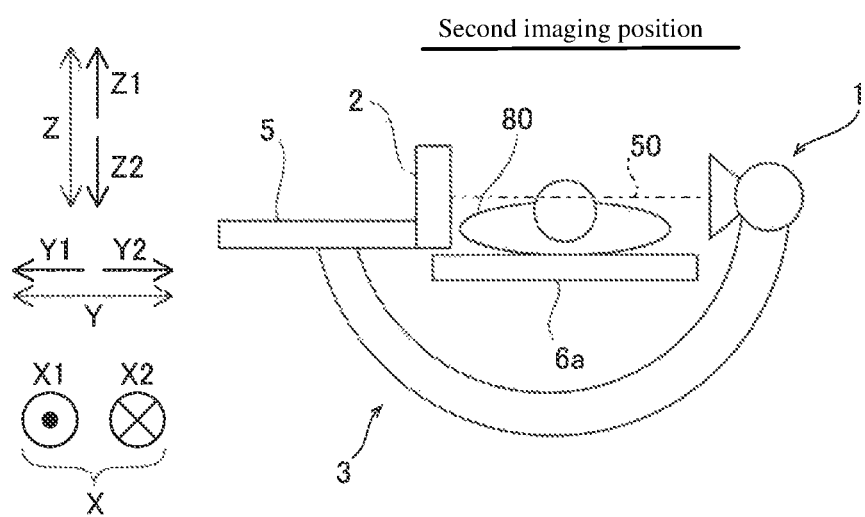
FIG. 6 is a schematic diagram for explaining a second imaging position.

Referring to FIG. 5 to FIG. 7, the control of the position adjustment operation when the imaging position is changed will be described. Hereinafter, as an example of the control of the imaging position adjustment operation, the control of the position adjustment operation when changing the first imaging position shown in FIG. 5 to the second imaging position shown in FIG. 6 will be described.

As shown in FIG. 5, the position in which the X-ray source 1 and the X-ray detector 2 are arranged such that the irradiation axis 50 extends along the Z-direction is defined as a first imaging position. The first imaging position is an imaging position for imaging the subject 80 from a direction along the direction of the body thickness 80*a* of the subject 80. Further, as shown in FIG. 6, the position at which the X-ray source 1 and the X-ray detector 2 are arranged such that the irradiation axis 50 extends in the direction along the Y-direction is defined as the second imaging position. That is, the second imaging position is an imaging position for imaging the subject 80 from a direction along the direction of the body width 80*b* (see FIG. 2) of the subject 80.

Figure 7A:
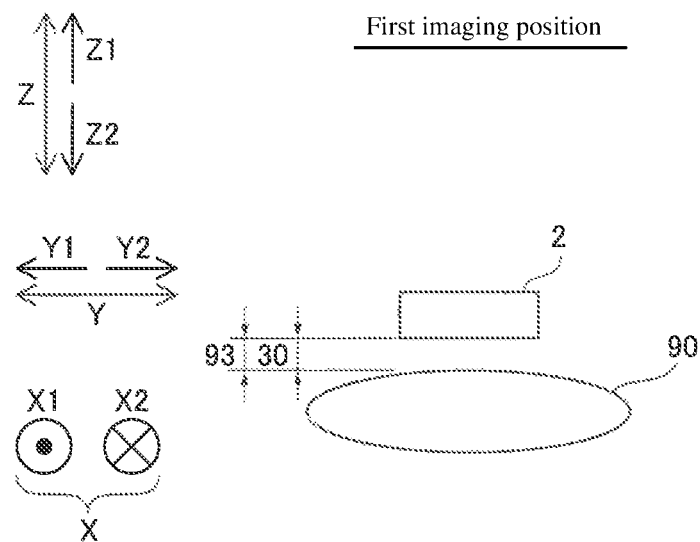
FIG. 7A is a schematic diagram for explaining the first imaging position in a position adjustment operation when an X-ray imaging apparatus according to one embodiment moves an arm automatically.

Referring to FIG. 7A to FIG. 7D, the control of the position adjustment operation when the imaging position is automatically changed from the first imaging position (see FIG. 5) to the second imaging position (see FIG. 6) will be described. FIG. 7A is a schematic diagram in which the X-ray detector 2 is placed at the first imaging position. As shown in FIG. 7A, the distance 30 between the X-ray detector 2 and the surface of the subject model 90 is a distance equal to the predetermined distance 93.

Figure 7B:
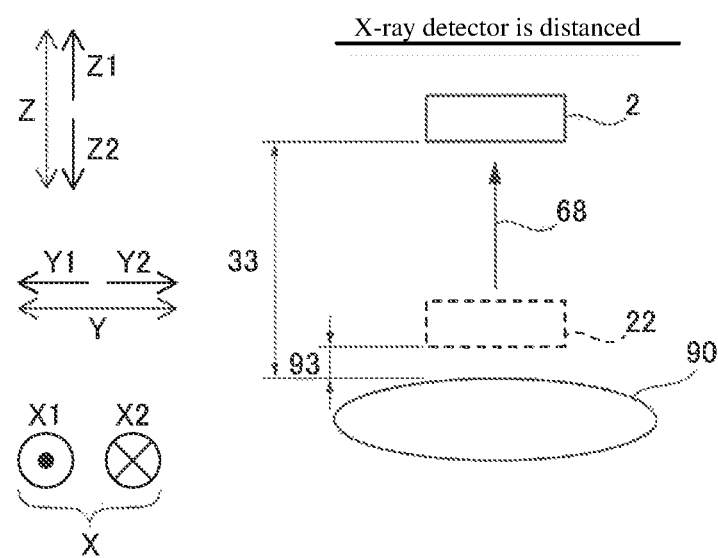
FIG. 7B shows a schematic diagram for explaining the operation of distancing the X-ray detector among position adjustment operations in a case where the X-ray imaging apparatus according to one embodiment moves the arm automatically.

As shown in FIG. 7B, the control unit 7 retracts the X-ray detector 2 by the X-ray detector moving mechanism 5 in advance or retracts the X-ray detector 2 while changing at least one of the position and the angle of the arm 3. Specifically, as shown by the arrow 68, the control unit 7 retracts the X-ray detector 2 from the position illustrated by the dashed line 22 to the position where the distance 30 from the X-ray detector 2 to the subject model 90 becomes the distance 33. Note that the distance 33 is a distance away from the subject model 90 to the extent that the X-ray detector 2 does not contact the subject 80 when moving the arm 3 (see FIG. 1) and is larger than the predetermined distance 93.

Figure 7C:
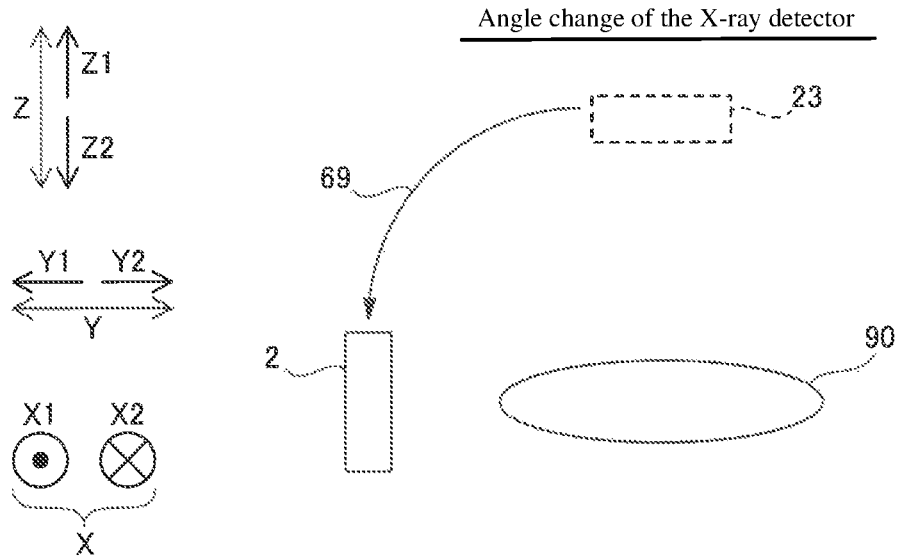
FIG. 7C is a schematic diagram for explaining the operation of changing the angle of the X-ray detector among position adjustment operations in a case where the X-ray imaging apparatus according to one embodiment moves the arm automatically.

Next, as shown in FIG. 7C, the control unit 7 rotates the arm 3 by controlling the arm driving mechanism 4 and the arm position change mechanism 10 to thereby rotate the X-ray detector 2 by 90 degrees from the position shown by the broken line 23 as shown by the arrow 69.

Figure 7D:
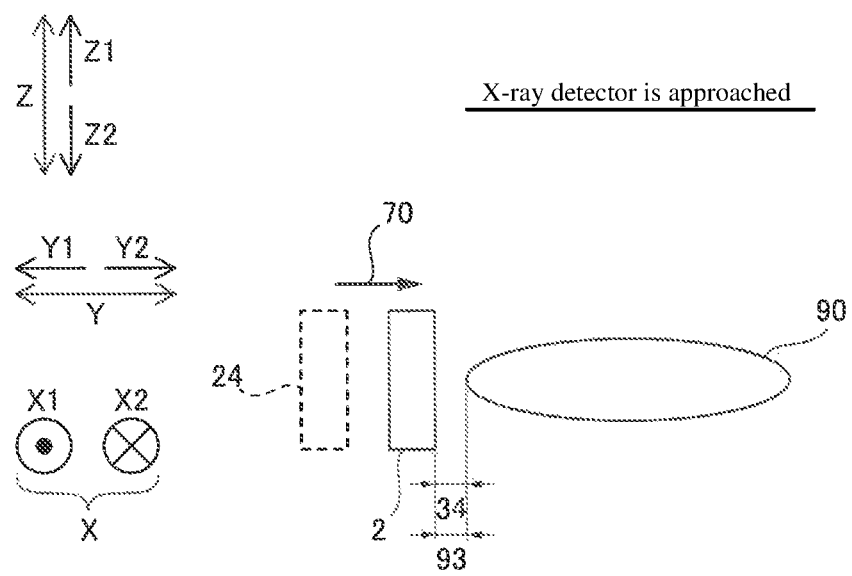
FIG. 7D is a schematic diagram for explaining the operation for bringing the X-ray detector closer among position adjustment operations in a case where the X-ray imaging apparatus according to one embodiment moves the arm automatically.

Next, as shown in FIG. 7D, the control unit 7 is configured to perform control of the position adjustment operation by advancing the X-ray detector 2 by the X-ray detector moving mechanism 5 after changing the imaging position or advancing the X-ray detector 2 while changing at least one of the position and the angle of the arm 3. In this embodiment, the control unit 7 is configured to perform control of the position adjustment operation by advancing the X-ray detector moving mechanism 5 after rotating the X-ray detector 2 by 90 degrees. Specifically, the control unit 7 moves the X-ray detector 2 from the position illustrated by the broken line 24 to the position where the distance 34 between the X-ray detector 2 and the surface of the subject model 90 at the imaging position after the change becomes a predetermined distance 93 in the Y2-direction as shown by the arrow 70. This completes the change from the first imaging position to the second imaging position. That is, the control unit 7 performs control of the position adjustment operation such that both of the distance 30 between the X-ray detector 2 and the subject model 90 before changing the imaging position and the distance 34 between the X-ray detector 2 and the surface of the subject model 90 at the position where the movement is completed become equal to the predetermined distance 93.

In this embodiment, the control unit 7 is configured to perform the control of the position adjustment operation in conjunction with the movement of the arm 3. Specifically, the control unit 7 acquires the position coordinate of the X-ray detector 2 before changing the imaging position, the position coordinate of the X-ray detector 2 after changing the imaging position, and the position coordinate of the subject model 90. Since the subject model 90 is arranged at the predetermined position on the top board 6*a*, the control unit 7 can acquire the position coordinate of the subject model 90 by acquiring the position coordinate of the top board 6*a*.

The control unit 7 is configured to perform the control for advancing the X-ray detector 2 or the control for retracting the X-ray detector 2, based on the position coordinate of the X-ray detector 2 after changing the imaging position and the position coordinate of the subject model 90.

(Position Adjustment Operation when Arm is Manually Moved)

Figure 8A:
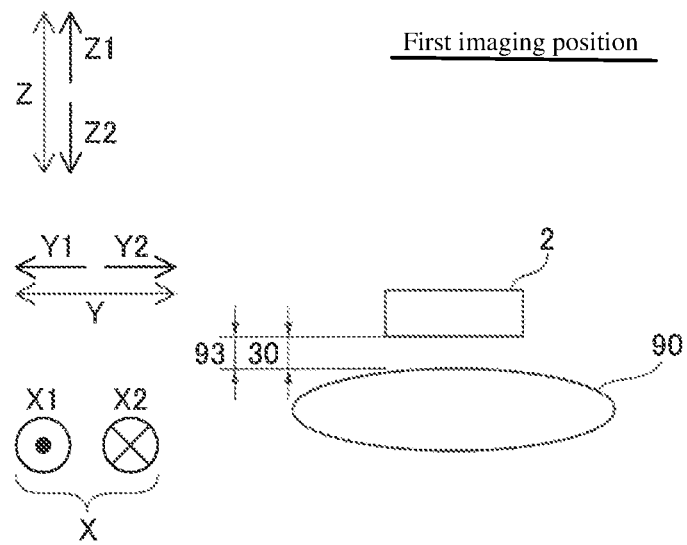
FIG. 8A is a schematic diagram for explaining a first imaging position in a position adjustment operation in a case where an operator manually moves the arm in the X-ray imaging apparatus according to one embodiment.

Referring to FIG. 8A to FIG. 8D, the control of the position adjustment operation when the arm 3 is moved manually from the first imaging position (see FIG. 5) to the second imaging position (see FIG. 6) will be described. FIG. 8A is a schematic diagram when the X-ray detector 2 is arranged at the first imaging position. As shown in FIG. 8A, the distance 30 between the X-ray detector 2 and the surface of the subject model 90 is equal to a predetermined distance 93.

The control unit 7 is configured to perform control of the position adjustment operation such that the X-ray detector 2 is moved along the surface of the subject model 90 in conjunction with the change of at least one of the position of the bed and the position and the angle of the arm 3 while the operator is changing at least one of the position of the bed 6 and the position and the angle of the arm 3.

Figure 8B:
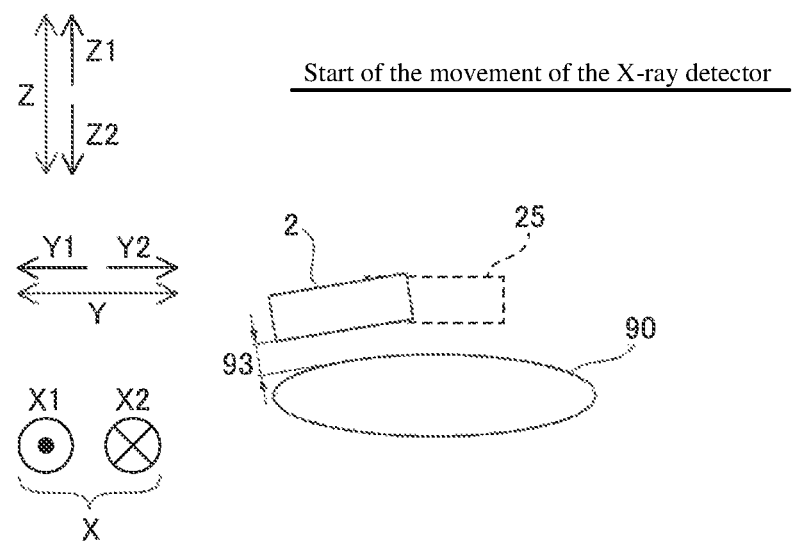
FIG. 8B is a schematic diagram for explaining the operation for starting the movement of the X-ray detector among position adjustment operations in a case where an operator manually moves the arm in the X-ray imaging apparatus according to one embodiment.
Figure 8C:
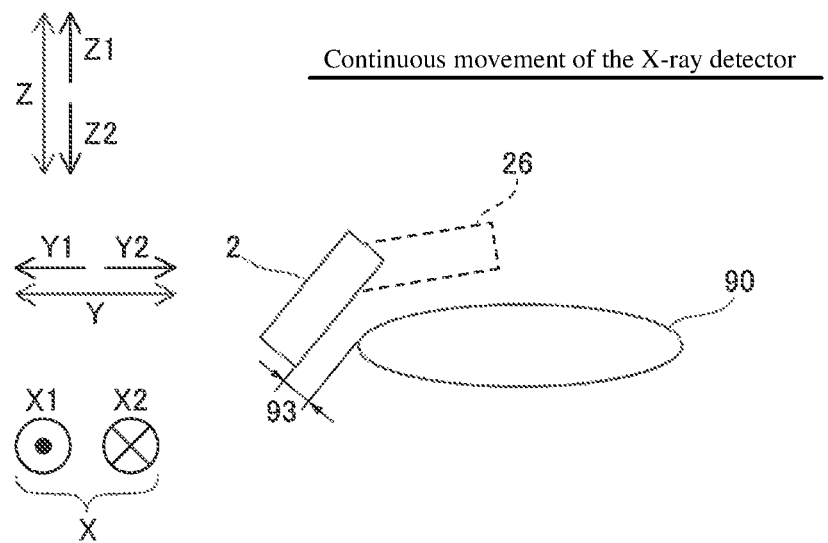
FIG. 8C is a schematic diagram for explaining the operation for continuously moving the X-ray detector among position adjustment operations in a case where an operator manually moves the arm in the X-ray imaging apparatus according to one embodiment.
Figure 8D:
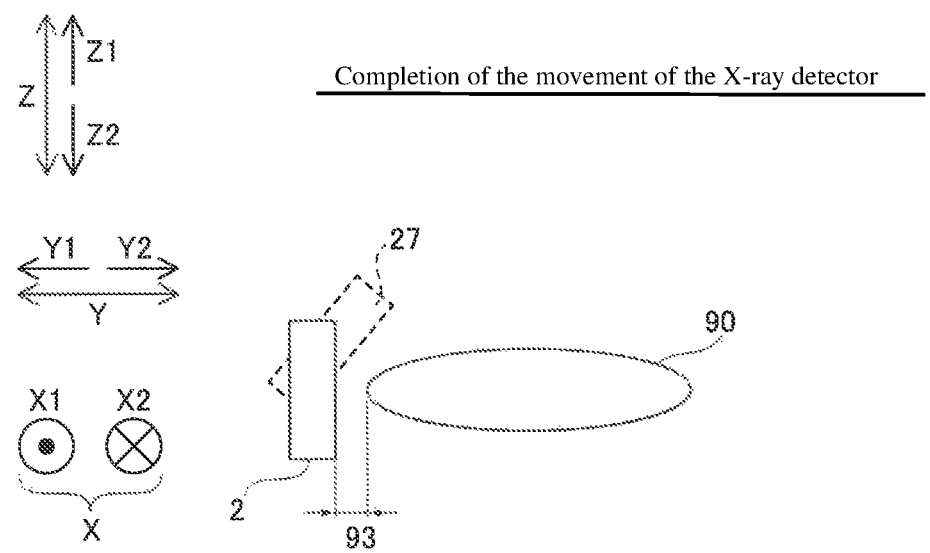
FIG. 8D is a schematic diagram for explaining the completion of the movement of the X-ray detector among position adjustment operations in a case where an operator manually moves the arm among the X-ray imaging apparatus according to one embodiment.

Specifically, as shown in FIG. 8B, the control unit 7 maintains the distance 30 between the X-ray detector 2 and the surface of the subject model 90 at a constant distance when the X-ray detector 2 begins to move from the position illustrated by the dashed line 25. That is, the control unit 7 maintains the distance 30 between the X-ray detector 2 and the surface of the subject model 90 at a predetermined distance 93. Further, as shown in FIG. 8C and FIG. 8D, when the X-ray detector 2 is moved from the position illustrated by the broken line 26 by changing the angle and the position of the X-ray detector 2, and even when the X-ray detector 2 is moved from the position illustrated by the broken line 27, the control unit 7 performs control of the position adjustment operation such that the distance 30 between the X-ray detector 2 and the subject model 90 at each position becomes the predetermined distance 93. That is, the control unit 7 is configured to continuously perform the control of the position adjustment operation such that at least one of the position of the bed 6 and the position and the angle of the arm 3 is changed based on the input operation of the operation and the X-ray detector 2 maintains the predetermined distance 93 with respect to the surface of the subject model 90 while the input operation of the operator is being performed.

(Switching Whether or not to Perform Control of Position Adjustment Operation)

Depending on the imaging site of the subject 80, there is a case in which the X-ray detector 2 is imaged with the X-ray detector 2 away from the subject 80. In this embodiment, the control unit 7 is configured to switch whether or not to perform the control of the position adjustment operation, based on the input operation of the operator.

Figure 9:
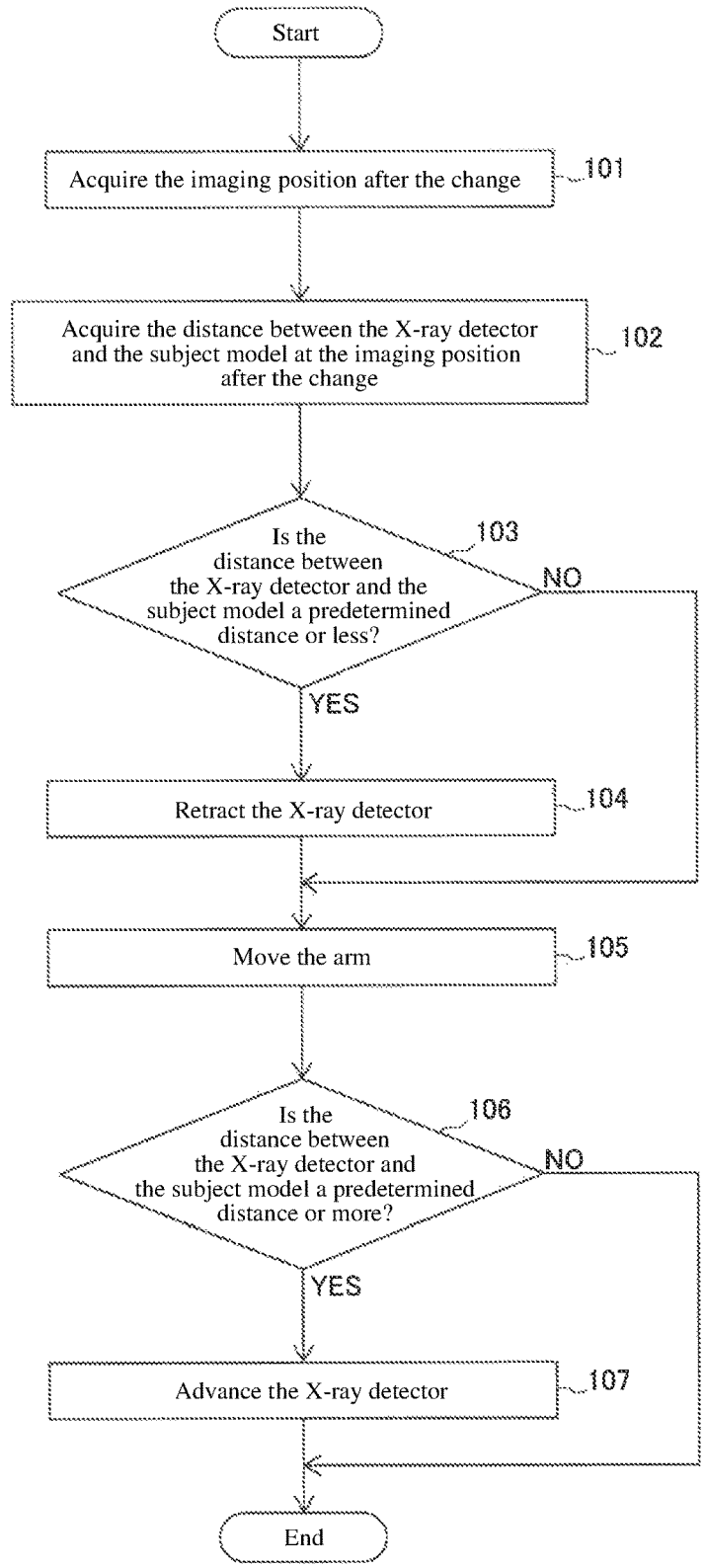
FIG. 9 is a flowchart for explaining the processing of the position adjustment operation when the X-ray imaging apparatus according to one embodiment automatically moves the arm.

Next, referring to FIG. 9, the processing of the control of the position adjustment operation when the arm 3 is automatically moved will be described. Note that this processing is started based on the input of the imaging position change by the operator. It is assumed that the subject model 90 is acquired in advance and stored in the storage unit 11.

In Step 101, the control unit 7 acquires the position of the X-ray detector 2 in the imaging position after the change. The control unit 7 acquires the position coordinate of the imaging position after the change to acquire the position of the X-ray detector 2 at the imaging position after the change.

In Step 102, the control unit 7 acquires the distance 30 between the X-ray detector 2 and the surface of the subject model 90 at the imaging position after the change. The control unit 7 acquires the distance 30 between the X-ray detector 2 and the surface of the subject model 90 at the imaging position after the change, based on the position coordinate of the imaging position after the change and the position coordinate of the subject model 90.

In Step 103, the control unit 7 determines whether or not the distance 30 between the X-ray detector 2 and the surface of the subject model 90 is the predetermined distance 93 or less. When the distance 30 between the X-ray detector 2 and the surface of subject model 90 is the predetermined distance 93 or less, the processing proceeds to Step 104. When the distance 30 between the X-ray detector 2 and the surface of the subject model 90 is the predetermined distance 93 or less, the processing proceeds to Step 105.

In Step 104, the control unit 7 controls the X-ray detector moving mechanism 5 to retract the X-ray detector 2. Specifically, the control unit 7 retracts the X-ray detector 2 to the position where the distance 30 between the X-ray detector 2 and the surface of the subject model 90 becomes the distance 33 (see FIG. 7).

In Step 105, the control unit 7 controls the arm driving mechanism 4 and the arm position change mechanism 10 to move the arm 3.

In Step 106, the control unit 7 determines whether or not the distance 30 between the X-ray detector 2 and the surface of the subject model 90 is a predetermined distance 93 or more. When the distance 30 between the X-ray detector 2 and the surface of the subject model 90 is the predetermined distance 93 or more, the processing proceeds to Step 107. When the distance 30 between the X-ray detector 2 and the surface of the subject model 90 is not the predetermined distance 93 or more, the processing ends.

In Step 107, the control unit 7 controls the X-ray detector moving mechanism 5 to advance the X-ray detector 2. Specifically, the control unit 7 advances the X-ray detector 2 to the position where the distance between the X-ray detector 30 and the surface of the subject model 90 becomes the predetermined distance 93. Thereafter, the processing ends.

Figure 10:
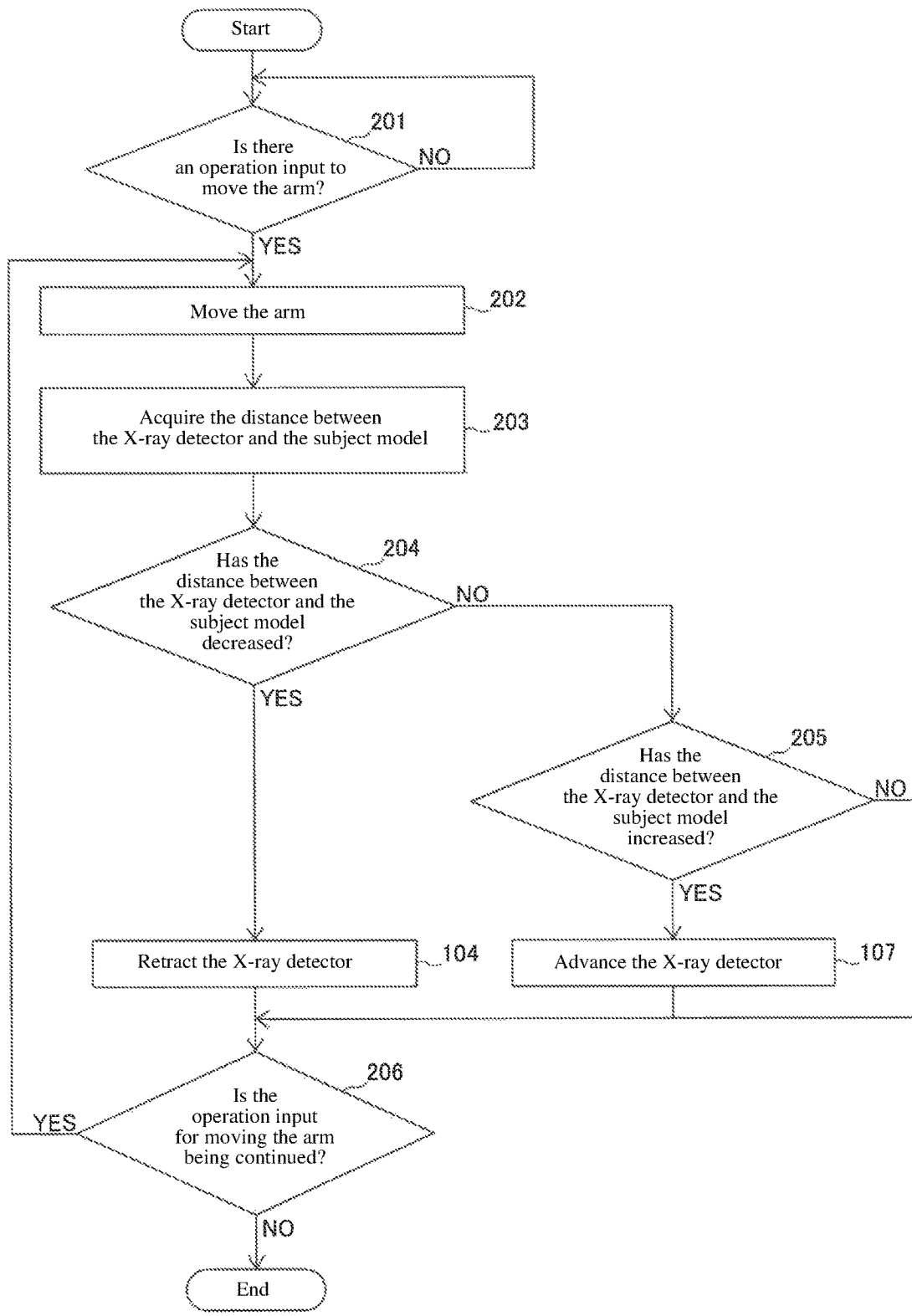
FIG. 10 is a flowchart for explaining the processing of the position adjustment operation in a case where an operator manually moves the arm in the X-ray imaging apparatus according to one embodiment.

Next, referring to FIG. 10, the processing of the control of the position adjustment operation when the operator manually moves the arm 3 will be described. Note that the same processing as in the processing of the control of the position adjustment operation when the arm 3 is automatically moved as shown in FIG. 9 is denoted by the same Step numerals, and the detailed descriptions thereof will be omitted.

In Step 201, the control unit 7 determines whether or not there is an operation input to move the arm 3. When there is an operation input to move the arm 3, the processing proceeds to Step 202. When there is no operation input to move the arm 3, the processing of Step 201 is continuously performed.

In Step 202, the control unit 7 controls the arm driving mechanism 4 and the arm position change mechanism 10 based on the operation input to move the arm 3. Note that the movement of the arm 3 in Step 202 is a movement by one clock of the processing of the control unit 7. That is, the moving distance of the arm 3 in Step 202 is a minute distance.

In Step 203, the control unit 7 acquires the distance 30 between the X-ray detector 2 and the surface of subject model 90.

In Step 204, the control unit 7 determines whether or not the distance 30 between the X-ray detector 2 and the surface of the subject model 90 has decreased. When the distance 30 between the X-ray detector 2 and the surface of the subject model 90 has decreased, the processing proceeds to Step 104. When the distance 30 between the X-ray detector 2 and the surface of the subject model 90 has not decreased, the processing proceeds to Step 205.

When the processing advances from Step 204 to Step 104, in Step 104, the control unit 7 controls the X-ray detector moving mechanism 5 to retract the X-ray detector 2. Thereafter, the processing proceeds to Step 206.

When the processing has proceeded from Step 204 to Step 205, in Step 205, the control unit 7 determines whether or not the distance 30 between the X-ray detector 2 and the surfaces of the subject model 90 has increased. When the distance 30 between the X-ray detector 2 and the surface of the subject model 90 has increased, the processing proceeds to Step 107. When the distance 30 between the X-ray detector 2 and the surface of the subject model 90 has not increased, the processing proceeds to Step 206.

In Step 107, the control unit 7 controls the X-ray detector moving mechanism 5 to advance the X-ray detector 2. Thereafter, the processing proceeds to Step 206.

In Step 206, the control unit 7 determines whether or not the operation input for moving the arm 3 is continuing. When the operation input for moving the arm 3 is not continued, the processing ends. When the operation input for moving the arm 3 is continuing, the processing proceeds to Step 202. In the processing of Step 206, the processing may be terminated based on the input of the operation input for terminating the movement of the arm 3. Further, either the processing of Step 204 and the processing of Step 104 or the processing of Step 205 and the processing of Step 108 may be performed first.

Figure 11:
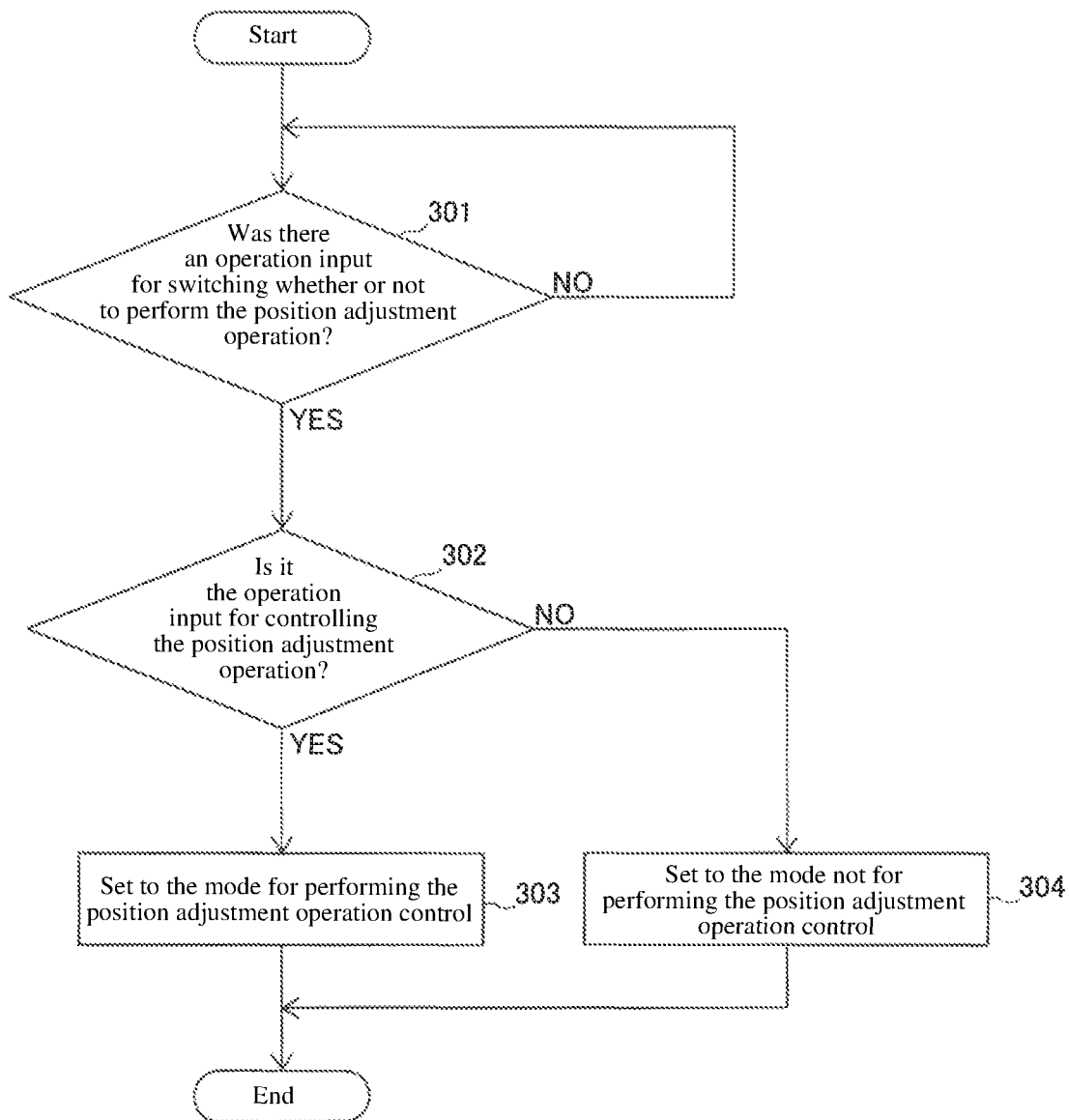
FIG. 11 is a flowchart for explaining the processing for switching whether or not to control the position adjustment operation in the X-ray imaging apparatus according to one embodiment.

Next, referring to FIG. 11, the processing will be described in which the control unit 7 switches whether or not the control unit 7 performs the control of the position adjustment operation.

In Step 301, the control unit 7 determines whether or not there is an operation input for switching whether or not to perform the control of the position adjustment operation. When there is an operation input for switching whether or not to perform the control of the position adjustment operation, the processing proceeds to Step 302. When there is no operation input for switching whether or not to perform the control of the position adjustment operation, the processing of Step 301 is repeated.

In Step 302, the control unit 7 determines whether or not the operation input inputted in Step 301 is an operation input for performing the control of the position adjustment operation. When the operation input is an operation input for performing the control of the position adjustment operation, the processing proceeds to Step 303. When the operation input is not an operation input for performing the control of the position adjustment operation, the processing proceeds to Step 304.

In Step 303, the control unit 7 sets a mode to the mode for performing the control of the position adjustment operation. Note that when the mode has been already set to the mode for performing the control of the position adjustment operation, the processing of Step 303 is skipped. Thereafter, the processing ends.

When the processing has proceeded from Step 302 to Step 304, in Step 304, the control unit 7 sets the mode to a mode not performing the control of the position adjustment operation. Note that the mode has been already set to the mode not performing the control of the position adjustment operation, the processing of Step 303 is skipped. Thereafter, the processing ends.

Effects of this Embodiment

In this embodiment, the following effects can be obtained.

In this embodiment, as described above, the X-ray imaging apparatus 100 is provided with the X-ray source 1 for irradiating the subject 80 with X-rays, the X-ray detector 2 for detecting X-rays emitted from the X-ray source 1, the arm 3 for holding the X-ray source 1 and the X-ray detector 2, the arm driving mechanism 4 for driving the arm 3, the X-ray detector moving mechanism 5 provided on the arm for advancing or retracting the X-ray detector 2 in the direction of the irradiation axis 50 of X-rays, the bed 6 for placing the subject 80 thereon, and the control unit 7. The control unit 7 performs the control of the position adjustment operation for adjusting the position of the X-ray detector 2 such that the distance 30 from the surface of the subject model 90 to the X-ray detector 2 by moving the X-ray detector 2 closer to the surface of the subject model 90, which is a model of the surface shape of the subject 80, or away from the surface of the subject model 90. Thus, by performing the control of the position adjustment operation, the X-ray detector 2 is placed at the position at the predetermined distance 93 from the front surface of the subject model 90. Therefore, the X-ray detector 2 can be brought closer to the subject 80, based on the distance between the subject 80 and the X-ray detector 2, considering the body shape of the subject 80 placed on the bed 6 rather than the distance between the X-ray detector 2 and the bed 6. Further, the X-ray detector 2 can be brought closer to the subject 80 without moving the X-ray detector 2 by the operator. As a result, it is possible to suppress the distance 30 between the subject 80 and the X-ray detector 2 from becoming larger than the predetermined distance 93 while suppressing the increase in the burden on the operator.

Further, in the above-described embodiment, the following further effects can be obtained by the following configuration.

In other words, in this embodiment, as described above, the control unit 7 is configured to acquire the body thickness 80a and the body width 80b of the subject 80 from the information 81 on the subject to generate the subject model 90. Thus, for example, the subject model 90 can be easily generated, as compared with the configuration in which the subject model 90 is generated by acquiring the three-dimensional data of the surface of the subject 80.

Further, in this embodiment, as described above, the control unit 7 is configured to acquire the body thickness 80a and the body width 80b of the subject 80 estimated from the height and the weight of the subject 80 as the information 81 on the subject. Thus, the body thickness 80a and the body width 80b of the subject 80 are estimated from the height and the weight of the subject 80. For this reason, the subject model 90 can be generated without actually measuring the body thickness 80a and the body width 80b of the subject 80 by the operator. As a result, the burden on the operator can be reduced.

Further, in this embodiment, as described above, the contact sensor 8 for detecting whether or not the X-ray detector 2 is brought into contact with the subject 80 is further provided. The control unit 7 is configured to regenerate the subject model 90, based on the position where the X-ray detector 2 and the subject 80 are brought into contact with each other detected by the contact sensor 8. As a result, the actual body thickness 80a and body width 80b of the subject 80 can be acquired based on the position of the X-ray detector 2 when the X-ray detector 2 is brought into contact with the subject 80. As a result, since the accuracy of the subject model 90 can be improved, the X-ray detector 2 can be brought closer to the subject 80.

Further, in this embodiment, as described above, the input receiving unit 9 for accepting an operation input by an operator is further provided. The control unit 7 is configured to generate the subject model 90, based on the body thickness level and the body width level of the subject 80 inputted by the input receiving unit 9. With this, the subject model 90 can be generated by selecting the body thickness level and the body width level by the operator. Thus, for example, even in a case where it is difficult to acquire the information 81 on the subject, such as, e.g., an emergency patient, the subject model 90 can be generated.

In this embodiment, as described above, the control unit 7 is configured to set the imaging condition based on the dose of the X-rays detected by the X-ray detector 2 and acquire the body thickness 80a and the body width 80b of the subject 80 based on the set imaging condition. As a result, the body thickness 80a and the body width 80b of the subject 80 are acquired based on the imaging condition. Therefore, by acquiring the imaging condition at the imaging position, the subject model 90 at the imaging position can be generated. Therefore, the accuracy of the subject model 90 at the imaging position can be improved.

In this embodiment, as described above, the arm driving mechanism 4 is configured to change the position and the angle of the arm 3 with respect to the bed 6. The control unit 7 is configured to perform the control of the position adjustment operation as follows. That is, when changing the imaging position by changing at least one of the position and the angle of the arm 3, the X-ray detector 2 is retracted in advance by the X-ray detector moving mechanism 5. Alternatively, the X-ray detector 2 is retracted while changing at least one of the position and the angle of the arm 3, and the X-ray detector 2 is advanced by the X-ray detector moving mechanism 5 after changing the imaging position. Alternatively, the X-ray detector 2 is advanced while changing at least one of the position and the angle of the arm 3. With this, by retracting the X-ray detector 2 in advance, it is possible to suppress the X-ray detector 2 from coming into contact with the subject 80 while the imaging position is being changed. Further, since the X-ray detector 2 is advanced after the change of the imaging position, the distance 30 between the X-ray detector 2 and the subject 80 can be prevented from increasing. As a result, it is possible to suppress the distance 30 between the X-ray detector 2 and the subject 80 from becoming large while suppressing the X-ray detector 2 from coming into contact with the subject 80 after the change of the imaging position.

Further, in this embodiment, as described above, the control unit 7 is configured to perform the control as follows. In the case of changing the imaging position, the control unit 7 acquires the imaging position after the change and acquires the distance 30 between the X-ray detector 2 and the surface of the subject model 90 at the imaging position after the change. When the acquired distance 30 between the X-ray detector 2 and the surface of the subject model 90 becomes the predetermined distance or less, the control unit 7 performs the control for retracting the X-ray detector 2. When the acquired distance 30 between the X-ray detector 2 and the surface of the subject model 90 becomes the predetermined distance or more, the control unit 7 performs the control for moving the X-ray detector 2. Accordingly, in the case of changing the imaging position, when the distance 30 between the X-ray detector 2 and the surface of the subject model 90 at the imaging position after the change deviates from the predetermined range, the position adjustment operation is performed. Therefore, it is possible to assuredly suppress the X-ray detector 2 from being arranged at the position where the distance 30 between the X-ray detector 2 and the subject 80 deviates the predetermined range.

Further, in this embodiment, as described above, the arm driving mechanism 4 is configured to change the position and the angle of the arm 3 with respect to the bed 6. The control unit 7 is configured such that the operator performs the control of the position adjustment operation as follows. That is, while at least one of the position of the bed 6 and the position and the angle of the arm 3 is changing, the control unit 7 performs control for moving the X-ray detector 2 along the surface of the subject model 90 in conjunction with at least one change in the position of the bed 6 and the position and the angle of the arm 3. With this, even in a case where the operator manually changes the position of the bed 6, and the position and the angle of the arm 3, the position adjustment operation is performed. Therefore, even in the case of manually moving the imaging position, the X-ray detector 2 can be brought closer to the subject 80 without requiring the operator to move the X-ray detector 2 closer to the subject 80. As a result, it is possible to suppress the increase in the burden on the operator.

Further, in this embodiment, as described above, the control unit 7 is configured to continuously perform the control of the position adjustment operation as follows. That is, while at least one of the position of the bed 6 and the position and the angle of the arm 3 is changed based on the input operation by the operator and the input operation by the operator is being performed, the X-ray detector 2 maintains the predetermined distance 93 with respect to the surface of the subject model 90.

With this, while the operator is moving at least one of the bed 6 and the arm 3, the distance 30 between the X-ray detector 2 and the surface of the subject model 90 is maintained at a predetermined distance 93. For this reason, for example, even in a case where the operator performs imaging while changing the imaging position by operating at least one of the bed 6 and the arm 3, it is possible to perform imaging while maintaining the state in which the X-ray detector 2 is close to the subject 80. As a result, even in the case of performing the imaging while changing the imaging position, the increase in the dose of X-rays can be suppressed, so that the increase in the exposure dose can be suppressed. Further, even in the case of performing the imaging while changing the imaging position, the increase in the dose of X-rays can be suppressed, so that the increase in the scattered X-rays can be suppressed. Consequently, even in the case of performing the imaging while changing the imaging position, it is possible to suppress the deterioration of the image quality of the resulting image due to the scattered X-rays.

Further, in this embodiment, as described above, the control unit 7 is configured to switch whether or not to perform the control of the position adjustment operation based on the input operation by the operator. With this, the position adjustment operation can be performed when the operator desires, and thus the convenience of the user can be improved.

Modifications

It should be understood that the embodiments disclosed here are examples in all respects and are not restrictive. The scope of the present invention is shown in claims rather than by the aforementioned embodiments, and the scope of the present invention includes all modifications (modified examples) within the meanings and scopes equivalent to the claims.

For example, in the above-described embodiment, an example is shown in which the X-ray imaging apparatus 100 generates the subject model 90 based on the information 81 on the subject, and the X-ray detector 2 is brought closer based on the generated subject model 90, but the present invention is not limited thereto. For example, as in the first modification shown in FIG. 12, the X-ray imaging apparatus 200 may be configured to update the subject model 90, based on the size of the subject model 90 and the relative position between the subject model 90 and the X-ray detector 2.

Figure 12:
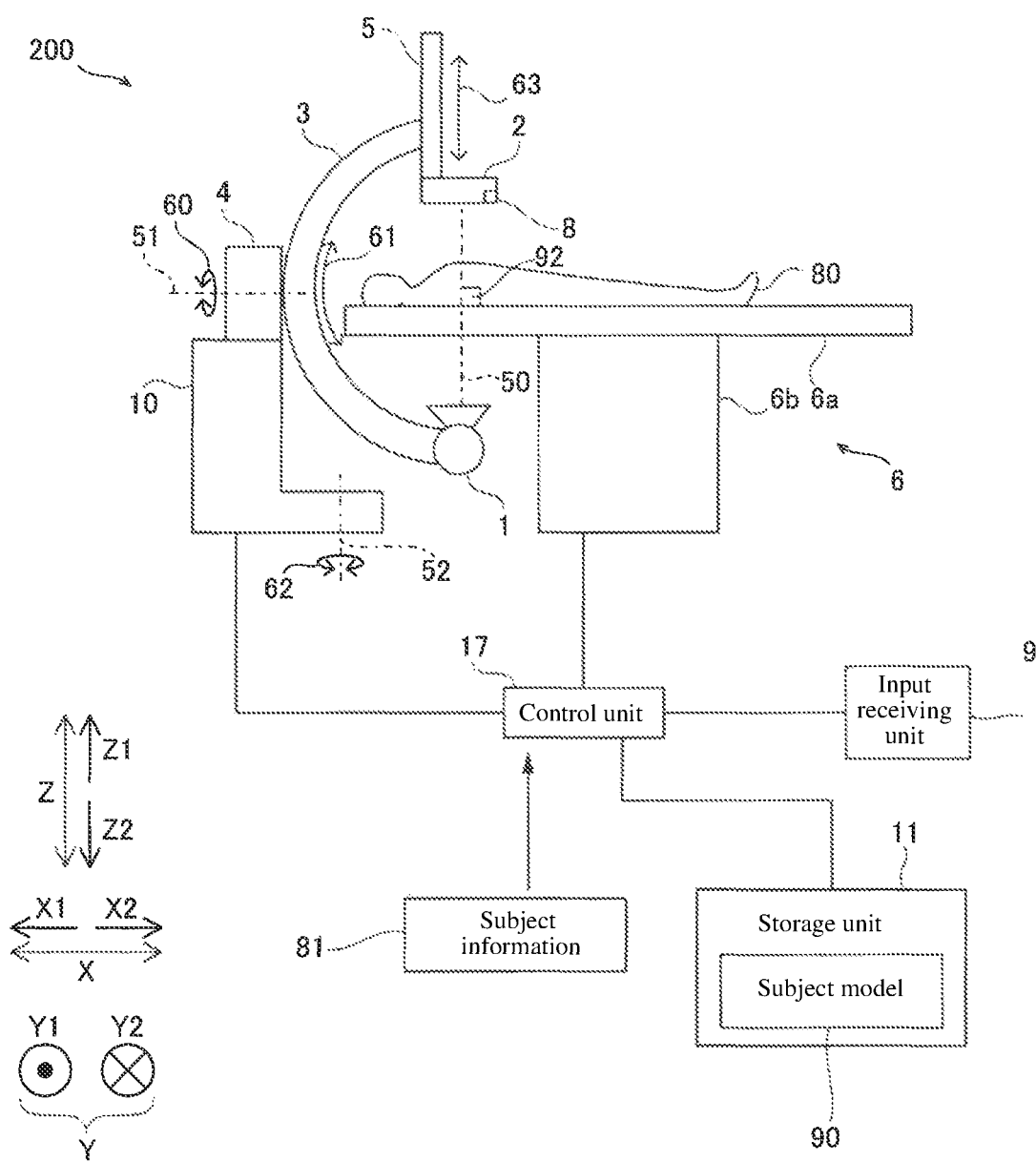
FIG. 12 is a schematic diagram showing the entire configuration of the X-ray imaging apparatus according to a first modification.

Specifically, as shown in FIG. 12, the X-ray imaging apparatus 200 according to the first modification differs from the X-ray imaging apparatus 100 according to the above-described embodiment in that it includes a control unit 17 instead of the control unit 7.

In the X-ray imaging apparatus 100 according to the above-described embodiment, the configuration is shown in which the subject model 90 is generated based on the information 81 on the subject. Here, the subject model 90 is generated by connecting a plurality of ellipses in the body axis direction of the subject 80. However, the size of each ellipse may differ from the size of the actual subject 80.

Thus, the control unit 17 according to the first modification is configured to regenerate the subject model 90, based on the size of the subject model 90 and the relative position between the subject model 90 and the X-ray detector 2. The control unit 17 according to the first modification causes the storage unit 11 to store the regenerated subject model 90.

That is, the control unit 17 according to the first modification is configured to update the subject model 90, based on the size of the subject model 90 and the relative position between the subject model 90 and the X-ray detector 2.

In the first modification, the control unit 17 determines that the size of the subject model 90 and the size of the subject 80 are different in a case where it is detected by the contact sensor 8 that the X-ray detector 2 and the subject 80 are brought into contact with each other when moving the X-ray detector 2 toward the surface of the subject model 90. When the size of the subject 80 is larger than the size of the subject model 90, the control unit 17 regenerates the subject model 90. When the size of the subject 80 is larger than the size of the subject model 90, the control unit 17 acquires the distance between the surface of the subject model 90 and the position where the X-ray detector 2 comes into contact with the subject 80 to regenerate the subject model 90.

Further, in a case where it is detected that the X-ray detector 2 is moved toward the surface of the subject model 90 and thereafter the X-ray detector 2 is further moved toward the subject 80 by the operator, the control unit 17 determines that the size of the subject model 90 is different from the size of the subject 80. The control unit 17 regenerates the subject model 90 when the size of the subject model 90 is larger than the size of the subject 80. In the first modification, the control unit 17 regenerates the subject model 90, based on the movement amount when moved further from the surface of the subject model 90.

Figure 13:
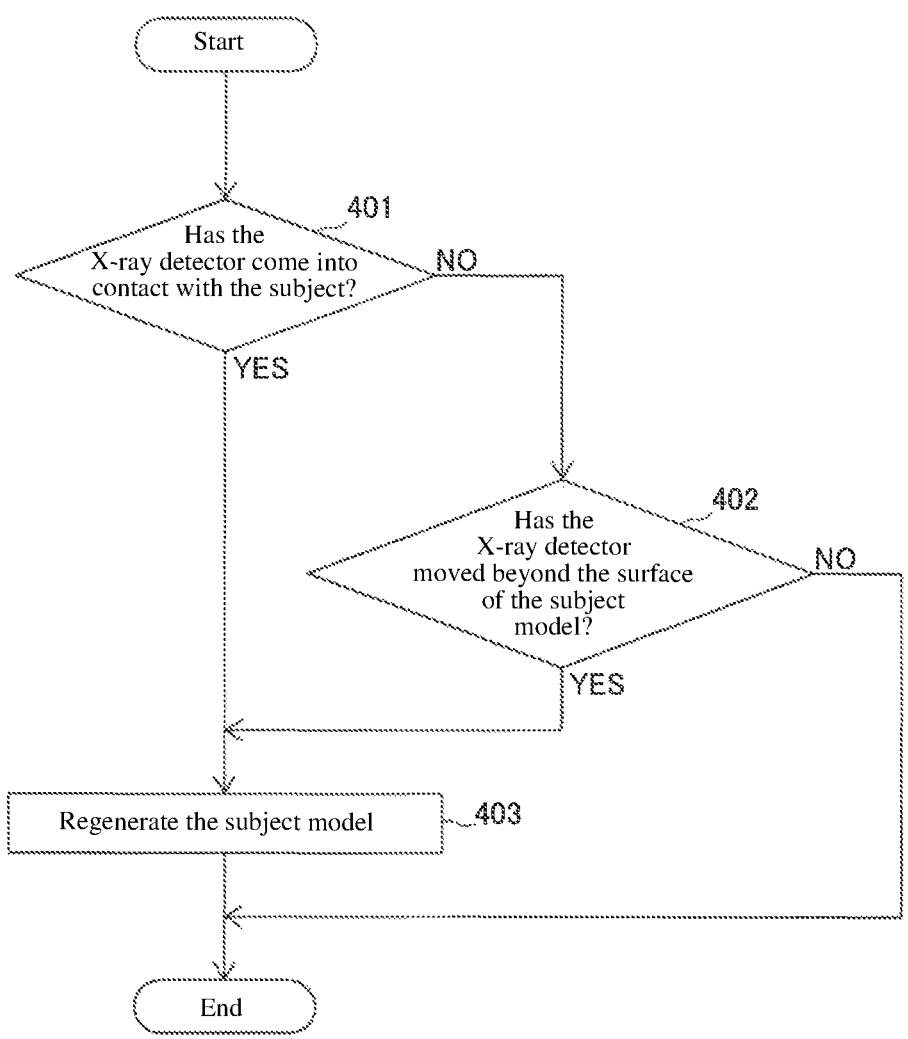
FIG. 13 is a flowchart for explaining the processing of regenerating a subject model according to a first modification.

Next, referring to FIG. 13, the processing will be described in which the control unit 17 regenerates the subject model 90. Note that the processing in which the control unit 17 regenerates the subject model 90 is executed while the position adjustment operation is being performed.

In Step 401, the control unit 17 determines whether or not the X-ray detector 2 has been brought into contact with the subject 80. When the X-ray detector 2 has not been in contact with the subject 80, the processing proceeds to Step 402. When the X-ray detector 2 comes into contact with the subject 80, the processing proceeds to Step 403

In Step 402, the control unit 17 determines whether or not the X-ray detector 2 has been moved beyond the subject model 90. When the X-ray detector 2 has been moved beyond the surface of the subject model 90, the processing proceeds to Step 403. When the X-ray detector 2 has not moved beyond the surface of the subject model 90, the processing ends. Note that the X-ray detector 2 has moved beyond the subject model 90 means that the X-ray detector 2 has moved from the surface of the subject model 90 toward the subject 80. That is, the X-ray detector 2 has moved beyond the subject model 90 means the state in which the X-ray detector 2 comes inside the subject model 90.

In Step 403, the control unit 17 regenerates the subject model 90. The control unit 17 updates the subject model 90 stored in the storage unit 11 by the subject model 90 regenerated in the processing of Step 403. Thereafter, the processing ends.

In the first modification, the control unit 17 repeatedly performs the processing of Step 401 to Step 403 every time the position adjustment operation is performed. The other configurations of the X-ray imaging apparatus 200 according to the first modification are the same as those of the X-ray imaging apparatus 100 according to the above-described embodiment.

In the first modification, as described above, the control unit 17 is configured to regenerate the subject model 90, based on the size of the subject model 90 and the relative position between the subject model 90 and the X-ray detector 2. Thus, the accuracy of the subject model 90 can be improved because the subject model 90 is regenerated based on the actual body thickness 80a and body width 80b of the subject 80. The other effects of the X-ray imaging apparatus 200 by the first modification are similar to the effects of the X-ray imaging apparatus 100 by the above-described embodiment.

Further, in the above-described embodiment, an example is shown in which the X-ray imaging apparatus 100 is provided with one arm 3, but the present invention is not limited thereto. For example, as in the second modification shown in FIG. 14, the X-ray imaging apparatus 300 may be provided with two arms 3.

Figure 14:
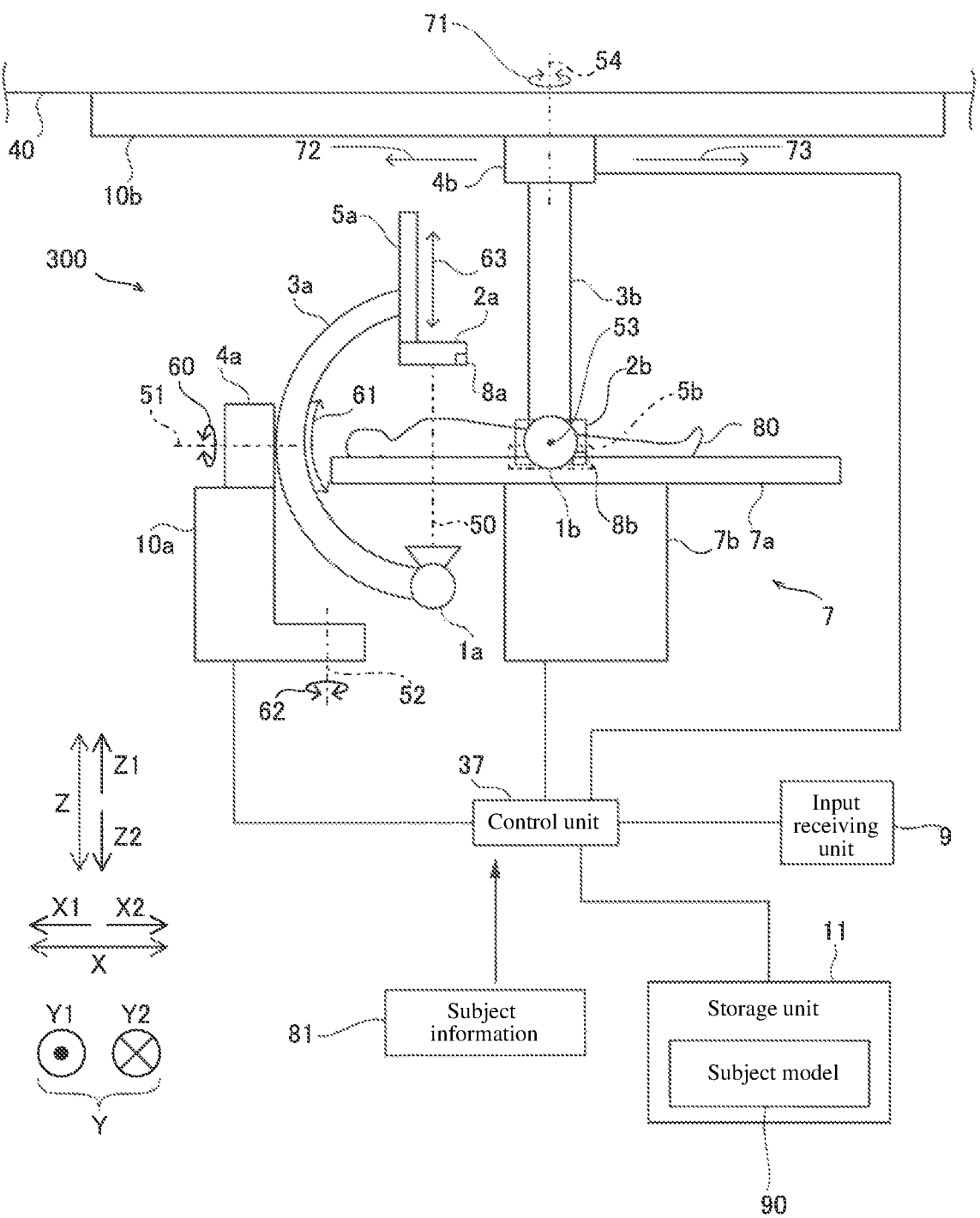
FIG. 14 is a schematic diagram showing the entire configuration of the X-ray imaging apparatus according to a second modification.

Specifically, as shown in FIG. 14, the X-ray imaging apparatus 300 according to the second modification differs from the X-ray imaging apparatus 100 according to the above-described embodiment in that it includes a control unit 37 instead of the control unit 7.

Further, in the X-ray imaging apparatus 300 according to the second modification, the X-ray source 1 includes a first X-ray source 1a and a second X-ray source 1b. In the X-ray imaging apparatus 300 according to the second modification, the X-ray detector 2 includes: a first X-ray detector 2a for detecting X-rays emitted from the first X-ray source 1a; and a second X-ray detector 2b for detecting X-rays emitted from the second X-ray source 1b.

The configurations of the first X-ray source 1a and the second X-ray source 1b are the same as those of the X-ray source 1 according to the above-described embodiment, and therefore, the detailed descriptions thereof will be omitted.

The configurations of the first X-ray detector 2a and the second X-ray detector 2b are those of the X-ray detector 2 according to the above-described embodiment, and therefore, the detailed description thereof will be omitted.

Further, in the X-ray imaging apparatus 300 according to the second modification, the arm 3 includes a first arm 3a for holding the first X-ray source 1a and the first X-ray detector 2a and a second arm 3b for holding the second X-ray source 1b and the second X-ray detector 2b. The configuration of the first arm 3a is the same as that of the arm 3 according to the above-described embodiment, and therefore, the detailed description thereof will be omitted. The second arm 3b holds the second X-ray source 1b and the second X-ray detector 2b. The second arm 3b is a so-called C-shaped arm. Further, the second arm 3b is held by the second arm driving mechanism 4b. In the example shown in FIG. 14, the second arm 3b is rotatably held by the second arm driving mechanism 4b. In the example shown in FIG. 14, the second arm 3b is arranged such that the long side of the bed 6 is positioned between the second X-ray source 1b and the second X-ray detector 2b.

Further, in the X-ray imaging apparatus 300 by the second modification, the arm driving mechanism 4 includes a first arm driving mechanism 4a for driving the first arm 3a, and a second arm driving mechanism 4b for driving the second arm 3b. The configuration of the first arm driving mechanism 4a is the same as that of the arm driving mechanism 4 according to the above-described embodiment, and therefore, the detailed description thereof will be omitted. The second arm driving mechanism 4b is configured so as to rotate the second arm 3b about the axis of the rotation axis 54 as shown by the arrow 71. In the example shown in FIG. 14, the second arm driving mechanism 4b is configured such that the rotation axis 54 extends in the up-down direction.

Further, the X-ray imaging apparatus 300 according to the second modification includes, as the arm position change mechanism 10, a first arm position change mechanism 10a and a second arm position change mechanism 10b. The configuration of the first arm position change mechanism 10a is the same as that of the arm 10 of the above-described embodiment, and therefore, the detailed descriptions thereof will be omitted. The second arm position change mechanism 10b is provided on the ceiling 40 of the examination room. The second arm position change mechanism 10b is configured to move the second arm driving mechanism 4b in the long axis direction of the bed 6 (the direction of the arrow 72 and the direction of the arrow 73). The second arm position change mechanism 10b includes a linear motion mechanism.

Further, in the second modification according to the X-ray imaging apparatus 300, the X-ray detector moving mechanism 5 is provided with a first X-ray detector moving mechanism 5a provided on the first arm 3a for moving the first X-ray detector 2a in the direction of the first irradiation axis 50 of the X-rays and a second X-ray detector moving mechanism 5b provided on the second arm 3b for moving the second X-ray detector 2b in the direction of the second irradiation axis 53 of the X-rays. In the example shown in FIG. 14, the second X-ray source 1b and the second X-ray detector 2b are provided such that the second irradiation axis 53 extends in the Y-direction. The configuration of the first X-ray detector moving mechanism 5a and the second X-ray detector moving mechanism 5b is the same as that of the X-ray detector moving mechanism 5 according to the above-described embodiment, and therefore, the detailed configuration will be omitted.

Further, the X-ray imaging apparatus 300 according to the second modification includes, as a contact sensor 8, a first contact sensor 8a and a second contact sensor 8b. The first contact sensor 8a is provided on the first X-ray detector 2a. The second contact sensor 8b is provided on the second X-ray detector 2b. The configurations of the first contact sensor 8a and the second contact sensor 8b are the same as those of the contact sensor 8 according to the above-described embodiment, and therefore, the detailed descriptions thereof will be omitted.

Further, in the X-ray imaging apparatus 300 according to the second modification, the control unit 37 is configured to perform the control of the first position adjustment operation and the control of the second position adjustment operation, as the control of the position adjustment operations. The control of the first position adjustment operation causes the position of the first X-ray detector 2a to be adjusted by advancing or retracting the first X-ray detector 2a such that the distance 30 from the surface of the subject model 90 to the first X-ray detector 2a becomes a predetermined distance 93. The control of the second position adjustment operation causes the position of the second X-ray detector 2b to be adjusted by advancing or retracting the second X-ray detector 2b such that the distance 30 from the surface of the subject model 90 to the second X-ray detector 2b becomes a predetermined distance 93.

The other configurations of the X-ray imaging apparatus 300 are the same as those of the X-ray imaging apparatus 100 according to the above embodiment.

In the second modification, as described above, the X-ray source 1 includes a first X-ray source 1a and a second X-ray source 1b. The X-ray detector 2 includes a first X-ray detector 2a for detecting X-rays emitted from the first X-ray source 1a and a second X-ray detector 2b for detecting X-rays emitted from the second X-ray source 1b. The arm 3 includes a first arm 3a for holding the first X-ray source 1a and the first X-ray detector 2a and a second arm 3b for holding the second X-ray source 1b and the second X-ray detector 2b. Further, the arm driving mechanism 4 includes the first arm driving mechanism 4a for driving the first arm 3a and the second arm driving mechanism 4b for driving the second arm 3b. Further, the X-ray detector moving mechanism 5 is provided with the first X-ray detector moving mechanism 5a provided on the first arm 3a for moving the first X-ray detector 2a in the direction of the first irradiation axis 50 of the X-rays and the second X-ray detector moving mechanism 5b provided on the second arm 3b for moving the X-ray second X-ray detector 2b in the direction of the second irradiation axis 53 of the X-rays. Further, the control unit 37 is configured to perform the control of the first position adjustment operation and performs the control of the second position adjustment operation. That is, the control of the first position adjustment operation causes the position of the first X-ray detector 2a to be adjusted such that the distance 30 from the surface of the subject model 90 to the first X-ray detector 2a becomes a predetermined distance 93 by advancing or retracting the first X-ray detector 2a. The control of the second position adjustment operation causes the position of the second X-ray detector 2b to be adjusted such that the distance 30 from the surface of the subject model 90 to the second X-ray detector 2b becomes a predetermined distance 93 by advancing or retracting the second X-ray detector 2b.

In the second modification, by configuring as described above, it becomes possible to bring the X-ray detector 2 closer to the subject 80 without moving the first X-ray detector 2a and the second the X-ray detector 2b by the operator. For this reason, it is preferable to apply the present invention to a so-called bi-plane imaging device provided with a first arm 3a and a second arm 3b. Other effects of the X-ray imaging apparatus 300 are similar to those of the X-ray imaging apparatus 100 by the above-described embodiment.

Further, in the above-described embodiment, an example is shown in which the control unit 7 performs the control for bringing the X-ray detector 2 closer to the surface of the subject model 90, as the control of the position adjustment operation, but the present invention is not limited thereto. For example, the control unit 7 may be configured to perform the control for bringing the X-ray detector 2 into close contact with the subject 80, as the position adjustment operation. With this configuration, for example, even in the case of performing the imaging the subject 80 in a state in which the X-ray detector 2 is in close contact with the subject 80, it is possible to perform imaging in a state in which the X-ray detector 2 is in close contact with the subject 80 without performing the operation for bringing the X-ray detector 2 into close contact with the subject 80 by the operator. As a result, it is possible to further suppress an increase in the burden on the operator.

Further, in the above-described embodiment, an example is shown in which the control unit 7 generates the subject model 90, but the present invention is not limited thereto. For example, the control unit 7 may be configured to acquire a subject model 90 generated in advance.

Further, in the above-described embodiment, an example is shown in which the control unit 7 is configured to be able to select any one of: a method of generating the subject model 90 based on the information 81 on the subject; a method of generating the subject model 90 based on the position where the X-ray detector 2 is brought into contact with the subject 80; a method of generating the subject model 90 based on the body thickness level and the body width level of subject 80 selected by the operator; and a method of generating the subject model 90 based on the body thickness 80*a* and the body width 80*b* of the subject 80 acquired based on the imaging condition, but the present invention is not limited thereto. For example, the control unit 7 may be configured to perform only one of: a method of generating the subject model 90 based on the information 81 on the subject; a method of generating the subject model 90 based on the position where the X-ray detector 2 is brought into contact with the subject 80; a method of generating the subject model 90 based on the body thickness level and the body width level of subject 80 selected by the operator; and a method of generating the subject model 90 based on the body thickness 80*a* and the body width 80*b* of the subject 80 acquired based on the imaging condition.

Further, in the above-described embodiment, an example is shown in which the control unit 7 performs the control of the position adjustment operation, based on the movement of the arm 3, but the present invention is not limited thereto. For example, the control unit 7 may be configured to perform the control of the position adjustment operation, based on the movement of the bed 6 (the top board 6*a*).

Further, in the above-described embodiment, an example is shown in which the control unit 7 acquires the body thickness 80*a* and the body width 80*b* of the subject 80 by acquiring the imaging condition, but the present invention is not limited thereto. For example, the control unit 7 may be configured to acquire the body thickness 80*a* and the body width 80*b* of the subject 80 based on the X-ray image captured by imaging the subject 80.

Further, in the above-described embodiment, an example is shown in which the control unit 7 is configured to generate the subject model 90 based on the height and weight of the subject 80, as the information 81 on the subject, but the present invention is not limited thereto. For example, the control unit 7 may be configured to acquire the three-dimensional data of the subject 80, which has been acquired in advance by CT (Computed Tomography), MM (Magnetic Resonance Imaging), as the information 81 on the subject, to thereby generate the subject model 90.

Further, in the above-described embodiment, an example is shown in which the control unit 7 generates a model having an elliptical shape as the subject model 90, but the present invention is not limited thereto. For example, the control unit 7 may store, as a subject model 90, a plurality of models in which the size of the short side and that of the long side are combined and may control to advance or retract the X-ray detector 2 based on the size of the short side and that of the long side of the model selected by the operator.

Further, in the above-described embodiment, an example is shown in which the X-ray imaging apparatus 100 is provided with a contact sensor 8, but the present invention is not limited thereto. For example, the X-ray imaging apparatus 100 may not include a contact sensor 8. In a case where the X-ray imaging apparatus 100 is not provided with a contact sensor 8, the contact sensor 8 may be replaced by a distance sensor. The control unit 7 may determine whether or not the X-ray detector 2 has been brought into contact with the subject 80 by the distance sensor.

Further, in the above-described embodiment, an example is shown in which the control unit 7 performs the control of the changing imaging position of the arm 3 to change the imaging position to the first imaging position and the second imaging position, but the present invention is not limited thereto. For example, the control unit 7 may perform the control for moving the arm 3 to an imaging position other than the first imaging position and the second imaging position. The imaging position may be set to any position.

Further, an example is shown in which the control unit 7 performs the control for moving the arm 3 to change the imaging position, but the present invention is not limited thereto. For example, the control unit 7 may be configured to change the imaging position by controlling the bed 6 without moving the arm 3. The control unit 7 may also be configured to change the imaging position by performing the control for moving both the arm 3 and the bed 6.

Further, in the above-described embodiment, an example is shown in which the control unit 7 performs the position adjustment operation such that the control unit 7 causes the X-ray detector 2 to retract by the X-ray detector moving mechanism 5 in advance and advance the X-ray detector 2 by the X-ray detector moving mechanism 5 after changing the imaging position, but the present invention is not limited thereto. For example, the control unit 7 may be configured to perform the position adjustment operation by retracting the X-ray detector 2 while changing at least one of the position and the angle of the arm 3 and advancing the X-ray detector 2 while changing at least one of the position and the angle of the arm 3.

Aspects

It will be understood by those skilled in the art that the above-described examples are concrete examples of the following aspects.

(Item 1)

An X-ray imaging apparatus comprising:
an X-ray source configured to irradiate a subject with X-rays;
an X-ray detector configured to detect the X-rays emitted from the X-ray source;
an arm configured to hold the X-ray source and the X-ray detector;
an arm driving mechanism configured to drive the arm;
an X-ray detector moving mechanism provided on the arm to advance or retract the X-ray detector in an irradiation axis direction of the X-rays;
a bed configured to place a subject thereon; and
a control unit,
wherein the control unit performs control of a position adjustment operation for adjusting a position of the X-ray detector such that a distance from a surface of a subject model serving as a model of a surface shape of the subject to the X-ray detector becomes a predetermined distance by moving the X-ray detector toward or away from the surface of the subject model.

(Item 2)

The X-ray imaging apparatus as recited in the above-described Item 1 wherein the control unit is configured to acquire a body thickness and a body width of the subject from information on the subject to generate the subject model.

(Item 3)

The X-ray imaging apparatus as recited in the above-described Item 1 wherein the control unit is configured to regenerate the subject model, based on a size of the subject model and a relative position between the subject model and the X-ray detector.

(Item 4)

The X-ray imaging apparatus as recited in the above-described Item 2 or 3.

wherein the control unit is configured to acquire, as the information on the subject, the body thickness and the body width of the subject estimated from a height and a weight of the subject.

(Item 5)

The X-ray imaging apparatus as recited in the above-described Item 2 or 3, further comprising:
a contact sensor configured to detect whether or not the X-ray detector and the subject have come into contact with each other,
wherein the control unit is configured to regenerate the subject model, based on a position of the X-ray detector detected by the contact sensor when the X-ray detector and the subject have come into contact with each other.

(Item 6)

The X-ray imaging apparatus as recited in the above-described Item 2 or 3, further comprising:
an input receiving unit configured to receive an operation input by an operator,
wherein the control unit is configured to generate the subject model, based on a body thickness level and a body width level of the subject inputted by the input receiving unit.

(Item 7)

The X-ray imaging apparatus as recited in the above-described Item 2 or 3,
wherein the control unit is configured to set an imaging condition based on a dose of X-rays detected by the X-ray detector and acquire the body thickness and the body width of the subject based on the set imaging condition.

(Item 8)

The X-ray imaging apparatus as recited in any one of the above-described Items 1 to 7,
wherein the arm driving mechanism is configured to change a position and an angle of the arm with respect to the bed, and
wherein when changing an imaging position by changing at least one of the position and the angle of the arm,
the control unit is configured to perform the control of the position adjustment operation by
retracting the X-ray detector by the X-ray detector moving mechanism in advance or retracting the X-ray detector while changing at least one of the position and the angle of the arm, and
advancing the X-ray detector by the X-rat detector moving mechanism after changing the imaging position or advancing the X-ray detector while changing at least one of the position and the angle of the arm.

(Item 9)

The X-ray imaging apparatus as recited in the above-described Item 8,
wherein when changing the imaging position,
the control unit is configured to perform
control for acquiring an imaging position after changing the imaging position, acquiring the distance between the X-ray detector and the surface of the subject model at the imaging position after changing the imaging position, and retracting the X-ray detector when the acquired distance between the X-ray detector and the surface of the subject model becomes the predetermined distance or less, and
control for advancing the X-ray detector when the acquired distance between the X-ray detector and the subject model becomes the predetermined distance or more.

(Item 10)

The X-ray imaging apparatus as recited in any one of the above-described Items 1 to 7,
wherein the arm driving mechanism is configured to change the position and the angle of the arm with respect to the bed, and
wherein the control unit performs the control of the position adjustment operation so as to move the X-ray detector along the surface of the subject model in conjunction with a change of at least one of the position of the bed, and the position and the angle of the arm, while an operator is changing at least one of the position of the bed, and the position and the angle of the arm.

(Item 11)

The X-ray imaging apparatus as recited in the above-described Item 10,
wherein the control unit is configured to continuously perform the control of the position adjustment operation such that at least one of the position of the bed, the position and the angle of the arm is changed, based on an input operation of the operator and that the X-ray detector maintains the predetermined distance with respect to the surface of the subject model while an input operation by the operator is being performed.

(Item 12)

The X-ray imaging apparatus as recited in any one of the above-described Items 1 to 11,
wherein the control unit is configured to perform, as the position adjustment operation, control for bringing the X-ray detector into close contact with the subject at an imaging position.

(Item 13)

The X-ray imaging apparatus as recited in any one of the above-described Items 1 to 12,
wherein the control unit is configured to switch whether or not to perform the control of the position adjustment operation, based on an input operation by an operator.

(Item 14)

The X-ray imaging apparatus as recited in any one of the above-described Items 1 to 13,
wherein the X-ray source includes a first X-ray source and a second X-ray source,
wherein the X-ray detector includes a first X-ray detector for detecting X-rays emitted from the first X-ray source and a second X-ray detector for detecting X-rays emitted from the second X-ray source,
wherein the arm includes a first arm for holding the first X-ray source and the first X-ray detector and a second arm for holding the second X-ray source and the second X-ray detector,
wherein the arm driving mechanism includes a first arm driving mechanism for driving the first arm and a second arm driving mechanism for driving the second arm,
wherein the X-ray detector moving mechanism includes a first X-ray detector moving mechanism provided on the first arm to move the first X-ray detector in a first irradiation axis direction of the X-rays and a second X-ray detector moving mechanism provided on the second arm to move the second X-ray detector in a second irradiation axis direction of the X-rays, and
wherein the control unit performs, as the control of the position adjustment operation,
control for a first position adjustment operation for adjusting a position of the first X-ray detector such that a distance between the surface of the subject model and the first X-ray detector becomes the predetermined distance by advancing or retracting the first X-ray detector, and control for a second position adjustment operation for adjusting a position of the second X-ray detector such that a distance between the surface of the subject model and the second X-ray detector becomes the predetermined distance by advancing or retracting the second X-ray detector.

The invention claimed is:

1. An X-ray imaging apparatus comprising:
an X-ray source configured to irradiate a subject with X-rays;
an X-ray detector configured to detect the X-rays emitted from the X-ray source;
an arm configured to hold the X-ray source and the X-ray detector;
an arm driving mechanism configured to rotate the arm;
an X-ray detector moving mechanism provided on the arm to advance or retract the X-ray detector in an irradiation axis direction of the X-rays from or to the arm;
a bed configured to place a subject thereon; and
a control unit,
wherein the control unit is configured to acquire a subject model serving as a model of a surface shape of the subject, and configured to perform position adjustment operation to move a position of the X-ray detector to an imaging position that is a predetermined distance away from the subject model, the position adjustment operation including controlling the arm driving mechanism to rotate the arm to a first orientation and controlling the X-ray detector moving mechanism to move the X-ray detector to the imaging position such that a distance from a surface of the subject model to the X-ray detector becomes the predetermined distance when the arm is at the first orientation after being rotated by the arm driving mechanism.

2. The X-ray imaging apparatus as recited in claim 1, wherein the control unit is configured to acquire a body thickness and a body width of the subject from information on the subject to generate the subject model.

3. The X-ray imaging apparatus as recited in claim 2, wherein the control unit is configured to generate the subject model based on the acquired body thickness and body width of the subject and to regenerate the subject model, based on a size of the subject model and a relative position between the subject model and the X-ray detector.

4. The X-ray imaging apparatus as recited in claim 1, wherein the arm driving mechanism is configured to change a position and an angle of the arm with respect to the bed, and
wherein when changing the imaging position from a first imaging position to a second imaging position by changing at least one of the position and the angle of the arm, the control unit is configured to perform the control of the position adjustment operation by:
retracting the X-ray detector by the X-ray detector moving mechanism in advance or retracting the X-ray detector while changing at least one of the position and the angle of the arm, and
advancing the X-ray detector by the X-ray detector moving mechanism after changing the imaging position or advancing the X-ray detector while changing at least one of the position and the angle of the arm.

5. The X-ray imaging apparatus as recited in claim 1, wherein the arm driving mechanism is configured to change a position and an angle of the arm with respect to the bed, and
wherein the control unit performs the control of the position adjustment operation so as to move the X-ray detector along the surface of the subject model in conjunction with a change of at least one of the position of the bed, and the position and the angle of the arm, while an operator is changing at least one of the position of the bed, and the position and the angle of the arm.

6. The X-ray imaging apparatus as recited in claim 1, wherein the control unit is configured to perform, as the position adjustment operation, control for bringing the X-ray detector into close contact with the subject at an imaging position.

7. The X-ray imaging apparatus as recited in claim 1, wherein the control unit is configured to switch whether or not to perform the control of the position adjustment operation, based on an input operation by an operator.

8. The X-ray imaging apparatus as recited in claim 1, wherein the X-ray source includes a first X-ray source and a second X-ray source,
wherein the X-ray detector includes a first X-ray detector for detecting X-rays emitted from the first X-ray source and a second X-ray detector for detecting X-rays emitted from the second X-ray source,
wherein the arm includes a first arm for holding the first X-ray source and the first X-ray detector and a second arm for holding the second X-ray source and the second X-ray detector,
wherein the arm driving mechanism includes a first arm driving mechanism for driving the first arm and a second arm driving mechanism for driving the second arm,
wherein the X-ray detector moving mechanism includes a first X-ray detector moving mechanism provided on the first arm to move the first X-ray detector in a first irradiation axis direction of the X-rays and a second X-ray detector moving mechanism provided on the second arm to move the second X-ray detector in a second irradiation axis direction of the X-rays, and
wherein the control unit performs, as the control of the position adjustment operation,
control for a first position adjustment operation for adjusting a position of the first X-ray detector such that a distance between the surface of the subject model and the first X-ray detector becomes the predetermined distance by advancing or retracting the first X-ray detector, and
control for a second position adjustment operation for adjusting a position of the second X-ray detector such that a distance between the surface of the subject model and the second X-ray detector becomes the predetermined distance by advancing or retracting the second X-ray detector.

9. The X-ray imaging apparatus as recited in claim 1, wherein the control unit is configured to perform the position adjustment operation to control the X-ray detector moving mechanism to move the X-ray detector to advance or retract after controlling the arm driving mechanism to rotate the arm to the first orientation such that the distance from the surface of the subject model to the X-ray detector at the imaging position becomes the predetermined distance when the arm is at the first orientation after being rotated by the arm driving mechanism.

10. The X-ray imaging apparatus as recited in claim 1, wherein the control unit is configured to perform the position adjustment operation to control the X-ray detector moving mechanism to move the X-ray detector to advance or retract in conjunction with controlling the arm driving mechanism to rotate the arm to the first orientation such that the distance from the surface of the subject model to the X-ray detector at the imaging position becomes the predetermined distance when the arm is at the first orientation after being rotated by the arm driving mechanism.

11. The X-ray imaging apparatus as recited in claim 2, wherein the control unit is configured to acquire, as the information on the subject, the body thickness and the body width of the subject estimated from a height and a weight of the subject.

12. The X-ray imaging apparatus as recited in claim 2, further comprising:
- a contact sensor configured to detect whether or not the X-ray detector and the subject have come into contact with each other,
- wherein the control unit is configured to regenerate the subject model, based on a position of the X-ray detector detected by the contact sensor when the X-ray detector and the subject have come into contact with each other.

13. The X-ray imaging apparatus as recited in claim 2, further comprising:
- an input receiving unit configured to receive an operation input by an operator,
- wherein the control unit is configured to generate the subject model, based on a body thickness level and a body width level of the subject inputted by the input receiving unit.

14. The X-ray imaging apparatus as recited in claim 2, wherein the control unit is configured to set an imaging condition based on a dose of X-rays detected by the X-ray detector and acquire the body thickness and the body width of the subject based on the set imaging condition.

15. The X-ray imaging apparatus as recited in claim 4, wherein when changing the imaging position, the control unit is configured to perform control for acquiring an instructed imaging position, acquiring the distance between the X-ray detector at the instructed imaging position and the surface of the subject model, retracting the X-ray detector toward the surface of the subject model to obtain the second imaging position in response to the acquired distance between the X-ray detector and the surface of the subject model being the predetermined distance or less, and advancing the X-ray detector away from the surface of the subject model to obtain the second imaging position in response to the acquired distance between the X-ray detector and the subject model being the predetermined distance or more.

16. The X-ray imaging apparatus as recited in claim 5, wherein the control unit is configured to continuously perform the control of the position adjustment operation such that at least one of the position of the bed, the position and the angle of the arm is changed, based on an input operation of the operator and that the X-ray detector maintains the predetermined distance with respect to the surface of the subject model while an input operation by the operator is being performed.

\* \* \* \* \*